US008524866B2

(12) United States Patent
Yang et al.

(10) Patent No.: US 8,524,866 B2
(45) Date of Patent: Sep. 3, 2013

(54) ANTIBODIES TO THE ALPHA-7 NICOTINIC RECEPTORS AND METHODS OF TREATING INFLAMMATORY DISORDERS WITH THE SAME

(75) Inventors: Lihong Yang, Manhasset, NY (US); Kevin J. Tracey, Old Greenwich, CT (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 1038 days.

(21) Appl. No.: 12/224,648

(22) PCT Filed: Nov. 15, 2006

(86) PCT No.: PCT/US2006/044329
§ 371 (c)(1),
(2), (4) Date: Apr. 7, 2009

(87) PCT Pub. No.: WO2007/059203
PCT Pub. Date: May 24, 2007

(65) Prior Publication Data
US 2009/0324588 A1  Dec. 31, 2009

Related U.S. Application Data

(60) Provisional application No. 60/737,045, filed on Nov. 15, 2005.

(51) Int. Cl.
*C07K 16/00* (2006.01)
*C12P 21/08* (2006.01)
*A61K 38/00* (2006.01)

(52) U.S. Cl.
USPC .......... 530/387.1; 530/387.2; 530/387.9; 530/389.1; 530/389.2; 514/1.4; 514/1.5; 514/1.7; 514/12.2; 514/16.6

(58) Field of Classification Search
None
See application file for complete search history.

(56) References Cited

U.S. PATENT DOCUMENTS

| 5,741,802 | A  | 4/1998  | Kem et al. |
| 5,902,814 | A  | 5/1999  | Gordon et al. |
| 5,977,144 | A  | 11/1999 | Meyer et al. |
| 5,998,429 | A  | 12/1999 | Macor et al. |
| 6,054,434 | A  | 4/2000  | Kropp et al. |
| 6,110,914 | A  | 8/2000  | Phillips et al. |
| 6,232,319 | B1 | 5/2001  | Marazano et al. |
| 6,323,000 | B2 | 11/2001 | Briggs et al. |
| 6,369,224 | B1 | 4/2002  | Phillips et al. |
| 6,407,095 | B1 | 6/2002  | Lochead et al. |
| 6,432,975 | B1 | 8/2002  | Schmitt et al. |
| 6,441,049 | B2 | 8/2002  | Reitz et al. |
| 6,479,172 | B2 | 11/2002 | Hu et al. |
| 6,479,510 | B2 | 11/2002 | Myers et al. |
| 6,486,172 | B2 | 11/2002 | Myers et al. |
| 6,492,385 | B2 | 12/2002 | Myers et al. |
| 6,492,386 | B2 | 12/2002 | Myers et al. |
| 6,500,840 | B2 | 12/2002 | Myers et al. |
| 6,538,003 | B1 | 3/2003  | Galli et al. |
| 6,552,012 | B2 | 4/2003  | Peters et al. |
| 6,562,816 | B2 | 5/2003  | Wishka et al. |
| 6,569,865 | B2 | 5/2003  | Eifion |
| 6,599,916 | B2 | 7/2003  | Myers et al. |
| 6,610,713 | B2 | 8/2003  | Tracey |
| 6,635,645 | B1 | 10/2003 | Lochead et al. |
| 6,838,471 | B2 | 1/2005  | Tracey |
| 7,238,715 | B2 | 7/2007  | Tracey et al. |
| 7,273,872 | B2 | 9/2007  | Tracey et al. |
| 7,785,808 | B2 | 8/2010  | Tracey et al. |
| 2001/0006796 | A1 | 7/2001 | Briggs et al. |
| 2002/0016344 | A1 | 2/2002 | Tracey |
| 2002/0040035 | A1 | 4/2002 | Myers et al. |
| 2002/0086871 | A1 | 7/2002 | O'Neill et al. |
| 2003/0105089 | A1 | 6/2003 | Wishka et al. |
| 2003/0119837 | A1 | 6/2003 | O'Neill et al. |
| 2003/0130305 | A1 | 7/2003 | Walker et al. |
| 2003/0149065 | A1 | 8/2003 | Loch, III et al. |
| 2003/0153595 | A1 | 8/2003 | Walker et al. |
| 2003/0176416 | A1 | 9/2003 | Peters et al. |
| 2003/0176702 | A1 | 9/2003 | Walker et al. |
| 2004/0204355 | A1 | 10/2004 | Tracey et al. |
| 2009/0123456 | A1 | 5/2009 | Tracey et al. |
| 2010/0256341 | A1 | 10/2010 | Tracey et al. |

FOREIGN PATENT DOCUMENTS

| CN | 1257500 A | 6/2000 |
| JP | 2002-030084 | 1/2002 |
| WO | WO 96/06098 | 2/1996 |
| WO | WO 97/30998 | 8/1997 |
| WO | WO 99/10338 | 3/1999 |
| WO | WO 01/73446 A1 | 10/2001 |

(Continued)

OTHER PUBLICATIONS

Gallowitsch-Puerta, 2005; Anna. N.Y. Acad. Science, vol. 1062; pp. 209-219.*
Lederman, 1991, Molecular Immunology, vol. 28, No. 11, pp. 1171-1181.*
Li, 1980, PNAS, vol. 77, No. 6, pp. 3211-3214.*
Barkas, 1987, Science, vol. 235, pp. 77-80.*
Alkondon, M., et al., "Choline is a Selective Agonist of ÿ7 Nicotinic Acetylcholine Receptors in the Rat Brain Neurons," *Eur. J. Neurosci.*, 9(12): 2734-2742 (1997).
Borovikova, et al., "Vagus Nerve Stimulation Attenuates the Systemic Inflammatory Response to Endotoxin," *Letters to Nature*, 405: 458-462 (2000).

(Continued)

*Primary Examiner* — Joanne Hama
*Assistant Examiner* — Ian Dang
(74) *Attorney, Agent, or Firm* — Hamilton, Brook, Smith & Reynolds, P.C.

(57) ABSTRACT

An antibody or an antigen binding fragment thereof which binds to mammalian α7 subunit of a nicotinic acetylcholine receptor or its functional variant and which is an agonist of said receptor or variant. Pharmaceutical compositions comprising same. A method of treating a subject suffering from an inflammatory condition comprising administering to said subject an antibody or an antigen-binding fragment as described herein.

33 Claims, 20 Drawing Sheets

(56) References Cited

FOREIGN PATENT DOCUMENTS

| WO | WO 01/85727 A1 | 11/2001 |
|---|---|---|
| WO | WO 01/89526 A1 | 11/2001 |
| WO | WO 02/76434 A2 | 3/2002 |
| WO | WO 02/44176 A1 | 6/2002 |
| WO | WO 02/057275 A1 | 7/2002 |
| WO | WO 03/032897 A2 | 4/2003 |
| WO | WO 03/032897 A3 | 4/2003 |
| WO | WO 03/078431 A1 | 9/2003 |
| WO | WO 2004/052365 A2 | 6/2004 |
| WO | WO 2007/059203 A2 | 5/2007 |

OTHER PUBLICATIONS

Broad, L. M., et al., "PSAB-OFP, a Selective ÿ7 Nicotinic Receptor Agonist, Is Also a Potent Agonist of the 5-HT3 Receptor," *Eur. J. Pharmacol.*, 452(2): 137-144 (2002).

Denham, W., et al., "Small Molecule Inhibition of Tumor Necrosis Factor Gene Processing During Acute Pancreatitis Prevents Cytokine Cascade Progression and Attenuates Pancreatitis Severity," *American Surgeon*, 63(12):1045-1050 (Dec. 1997).

Francis, M. M., et al., "Specific Activation of the ÿ7 Nicotinic Acetylcholine Receptor by a Quaternary Analog of Cocaine," *Mol. Pharmacol.*, 60(1): 71-79 (2001).

Holladay, M. W., et al., "Neuronal Nicotinic Acetylcholine Receptors as Targets for Drug Discovery," *J. Med. Chem.* 40(26):4169-4194 (Dec. 1997).

Kem, W. R., "The brain ÿ7 nicotinic receptor may be an important therapeutic target for the treatment of Alzheimer's disease: studies with DMXBA (GTS-21)," *Behav. Brain Res.*, 113: 169-181 (2000).

Levin, E. D., et al., "AR-R17779, An ÿ7 Nicotinic Agonist, Improves Learning and Memory in Rats," *Behav. Pharmacol.*, 10(6-7): 675-680 (1999).

Meyer, E. M., et al., "3-[2,4-Dimethoxybenzylidene]Anabaseine (DMXB) Selectively Activates Rat ÿ7 Receptors and Improves Memory-Related Behaviors in a Mecamylamine-Sensitive Manner," *Brain Res.*, 768(1-2): 49-56 (1997).

Moreland, L. W. et al., "Treatment of Rheumatoid Arthritis With a Recombinant Human Tumor Necrosis Factor Receptor (p75)-Fc Fusion Protein," *The New England Journal of Medicine*, 337(3): 141-147 (Jul. 17, 1997).

Mullen, G., et al., "(ÿ)-Spiro[1-azabicyclo[2.2.2]octane-3,5'-oxazolidin-2'-one], a Conformationally Restricted Analogue of Acetylcholine, Is a Highly Selective Full Agonist at the ÿ7 Nicotinic Acetylcholine Receptor," *J. Med. Chem.*, 43(22): 4045-4050 (2000).

Nanri, M., et al., "GTS-21, a Nicotinic Agonist, Attenuates Multiple Infarctions and Cognitive Deficit Caused by Permanent Occlusion of Bilateral Common Carotid Arteries in Rats," *Jpn. J. Pharmacol.*, 78, pp. 463-469 (1998).

Nanri, M., et al., "Protective Effect of GTS-21, a Novel Nicotinic Receptor Agonist, on Delayed Neuronal Death Induced by Ischemia in Gerbils," *Jpn. J. Pharmacol. 76*, pp. 23-29 (1998).

Pavlov, V. A., et al., "The Cholinergic Anti-Inflammatory Pathway: A Missing Link in Neuroimmunomodulation," *Molecular Medicine*, 9(5-8): 125-134 (2003).

Pereira, E. F. R., et al., "Identification and Functional Characterization of a New Agonist Site on Nicotinic Acetylcholine Receptors of Cultured Hippocampal Neurons," *J. Pharmacology and Experimental Therapeutics* 265(3):1474-1491 (1993).

Shimohama, S., et al., "Nicotinic α 7 Receptors Protect Against Glutamate Neurotoxicity and Neuronal Ischemic Damage," *Brain Research 779*, pp. 359-363 (1998).

Tamamizu, S. et al., "Effects of Antibody Binding on Structural Transitions of the Nicotinic Acetylcholine Receptor," *Biochemistry* 35:11773-11781 (1996).

Tracey, Kevin J., et al., "Mind Over Immunity," *FESEB J.*, 15(9): 1575-1576 (2001).

Tzartos, S. J., et al., "The Main Immunogenic Region (MIR) of the Nicotinic Acetylcholine Receptor and the Anti-MIR Antibodies," *Molecular Neurobiology* 5:1-29 (1991).

Wang, H., et al., "Nicotinic Acetylcholine Receptor α7 Subunit Is an Essential Regulator of Inflammation," *Nature*, pp. 1-4 (2002).

Wang, H., et al., "Nicotinic acetylcholine receptor α7 subunit is an essential regulator of inflammation," *Nature* 421:384-388 (Jan. 2003).

European Search Report for Application No. EP 07020473, Date of Mailing Sep. 17, 2008.

Office Action from Application No. EP 07020473.0, dated May 14, 2009.

Partial European Search Report from Application No. EP 07020473.0, dated Jun. 24, 2008.

Notification of Transmittal of the International Search Report (ISR) and the Written Opinion (WO) of the International Searching Authority, or the Declaration, with ISR and WO, PCT/US2006/044329, mailed Jan. 6, 2007.

Notification concerning Transmittal of International Preliminary Report on Patentability (IPRP) with IPRP, PCT/US2006/044329, mailed May 29, 2008.

Office Action from Application No. EP 09001425.9, dated May 13, 2009.

Office Action with European Search Report from EP 09 001 425.9, dated Apr. 27, 2009.

Office Action from Application No. CN 200380108261.5, dated Jun. 26, 2009 (with English translation).

Office Action from EP 06 837 656.5, dated May 19, 2009.

Notification of Transmittal of the International Preliminary Examination Report (IPER) with IPER, PCT/US03/38708, dated Dec. 27, 2004.

Written Opinion, PCT/US03/38708, dated Aug. 31, 2004.

Notification of Transmittal of the International Search Report (ISR) or the Declaration with ISR, PCT/US03/38708, dated Aug. 9, 2004.

Invitation to Pay Additional Fees, PCT/US03/38708, dated May 17, 2004.

Reply, Application No. EP 09001425.9, filed Sep. 22, 2009.

Communication pursuant to Article 94(3) EPC, EP 09001425.9, dated Nov. 17, 2009.

Office Action with English translation of text, China 200680050315.0, dated Oct. 11, 2010.

Reply, EP 09001425.9, filed May 25, 2010.

Office Action, U.S. Appl. No. 11/724,605, dated Jul. 29, 2009.

Reply, U.S. Appl. No. 11/724,605, filed Nov. 30, 2009.

Notice of Allowance, U.S. Appl. No. 11/724,605, dated Mar. 22, 2010.

Office Action, U.S. Appl. No. 12/818,347, dated Mar. 30, 2011.

Communication pursuant to Article 94(3) EPC, EP 09 001 425.9, dated Mar. 1, 2011.

Johnson, D.S. et al., "Alpha-Conotoxin ImI Exhibits Subtype-Specific Nicotinic Acetylcholine Receptor Blockade: Preferential Inhibition of Homomeric Alpha 7 and alpha 9 Receptors", *Mol Pharmacol.* 48(2): Abstract (1995).

Matsunaga, K. et al., "Involvement of Nicotinic Acetylcholine Receptors in Suppression of Antimicrobial Activity and Cytokine Responses of Alveolar Macrophages to *Legionella pneumophila* Infection by Nicotine", *J. Immunology 167*: 6518-6524 (2001).

Messer, Jr., M.D., William S., "MBC 3320 Acetylcholine", The University of Toledo, (2001).

Toyabe, S. et al., "Identification of Nicotinic Acetylcholine Receptors on Lymphocytes in the Periphery as well as Thymus in Mice", *Immunology 92*: 201-205 (1997).

Van Maanen, M.A. et al., "Stimulation of Nicotinic Acetylcholine Receptors Attenuates Collagen-Induced Arthritis in Mice", *Arthritis & Rheumatism 60*(1): 114-122 (2009).

Office Action, China 200680050315.0, dated Jun. 10, 2011 with Eng. translation.

Reply, U.S. Appl. No. 12/818,347, filed Aug. 30, 2011.

Reply, EP 09 011 425.9, filed Aug. 9, 2011.

Final Office Action, U.S. Appl. No. 12/818,347, dated Nov. 21, 2011.

Reply, U.S. Appl. No. 12/818,347, filed Mar. 21, 2012.

Office Action, JP 2008-541306, mailed Mar. 2, 2012.

\* cited by examiner

```
  1  mrcspggvwl alaasllhvs lqgefqrkly kelvknynpl erpvandsqp ltvyfslnll
 61  qimdvdeknq vlttniwlqm swtdhylqwn vseypgvktv rfpdgqiwkp dillynsade
121  rfdatfhtnv lvnpsghcqy lppgifkssc yidvrwfpfd vqhcklkfgs wsyggwsldl
181  qmqeadisgy ipngewdlvg ipgkrserfy ecckepypdv tftvtmrrrt lyyglnllip
241  cvlisalall vfllpadsge kislgitvll sltvfmllva eimpatsdsv pliaqyfast
301  miivglsvvv tvivlqyhhh dpdggkmpkw trvillnwca wflrmkrpge dkvrpacqhk
361  qrrcslasve msavapppas ngnllyigfr gldgvhcvpt pdsgvvcgrm acspthdehl
421  lhggqppegd pdlakileev ryianrfrcq deseavcsew kfaacvvdrl clmafsvfti
481  ictigilmsa pnfveavskd fa
```

ANTIBODIES TO THE ALPHA-7 NICOTINIC RECEPTORS AND METHODS OF TREATING INFLAMMATORY DISORDERS WITH THE SAME

RELATED APPLICATIONS

This application is the U.S. National Stage of International Application No. PCT/US2006/044329, filed Nov. 15, 2006, published in English, which claims the benefit of U.S. Provisional Application No. 60/737,045, filed Nov. 15, 2005. The entire teachings of the above applications are incorporated herein by reference.

BACKGROUND OF THE INVENTION

Mammals respond to inflammation in part through central nervous system regulation. One set of responses is through efferent vagus nerve signaling, termed the "cholinergic anti-inflammatory pathway" (Borovikova et al., Vagus nerve stimulation attenuates the systemic inflammatory response to endotoxin. *Nature:* 405:458-462 (2000)). Stimulation of the efferent vagus nerve or signaling through α-bungarotoxin-sensitive nicotinic acetylcholine receptors (by, e.g., acetylcholine) attenuates systemic inflammatory responses and macrophage cytokine synthesis (Bernik, T. R. et al. Pharmacological stimulation of the cholinergic anti-inflammatory pathway. J. Exp. Med. 195:781-788 (2002); Tracey et al. Mind over immunity. FASEB J. 15:1575-1576 (2001); U.S. patent application Ser. No. 09/855,446).

Nicotinic acetylcholine receptors are a family of ligand-gated, pentameric ion channels. In humans, 16 different subunits (α1-7, α9-10, β1-4, δ, ε, and γ) have been identified that form a large number of homo- and hetero-pentameric receptors with distinct structural and pharmacological properties (Lindstrom, 1995; Leonard and Bertrand, 2001; Le Novere and Changeux, 1995). The main known function of this receptor family is to transmit signals for the neurotransmitter acetylcholine at neuromuscular junctions and in the central and peripheral nervous systems (Lindstrom, J. M. Nicotinic acetylcholine receptors. In "Hand Book Of Receptors And Channels: Ligand- And Voltage-Gated Ion Channels." Edited by R. Alan North. CRC Press, Inc. (1995); Leonard, S. and Bertrand, D. Neuronal nicotinic receptors: from structure to function. Nicotine & Tobacco Res. 3:203-223 (2001); Le Novere, N. & Changeux, J-P. Molecular evolution of the nicotinic acetylcholine receptor: an example of multigene family in excitable cells. J. Mol. Evol. 40:155-172 (1995); Marubio, L. M. and Changeux, J-P. Nicotinic acetylcholine receptor knockout mice as animal models for studying receptor function. Eur. J. Pharmacol. 393:113-121 (2000); Steinlein, O. New functions for nicotine acetylcholine receptors? Behavioural Brain Res. 95:31-35 (1998)).

In a co-pending Published U.S. Patent Application No. 2004/0204355, the identity of the subunit of an acetylcholine receptor primarily responsible for attenuation of inflammatory responses was disclosed to be the α7 subunit. However, the mechanisms through which the α7 subunit acts and that would facilitate design of novel anti-inflammatory pharmaceutical agents remained unknown.

There is, however, a continued need for pharmaceutically active agents that can exploit the cholinergic anti-inflammatory pathway by activating acetylcholine receptor in a type-specific manner with minimal side effects.

SUMMARY OF THE INVENTION

The present invention is based on the discovery that the cholinergic anti-inflammatory pathway can be activated by binding to specific regions of the α7 subunit of a nicotinic receptor. Specifically, Applicants have discovered that the cholinergic anti-inflammatory pathway is activated upon binding to an α7 nicotinic receptor by antibodies cognate to certain fragments of the receptor (Examples 4-7). Based on this discovery, novel antibodies and pharmaceutical compositions comprising the same useful for treatment of inflammatory conditions are disclosed.

In one embodiment, the present invention is an isolated antibody or an antigen binding fragment thereof that specifically binds to a peptide consisting of an amino acid sequence having at least 80% identity to a sequence selected from the group of SEQ ID NO:2, SEQ ID NO:3 and SEQ ID NO:4.

In one embodiment, the present invention is isolated antibody or an antigen-binding fragment thereof that specifically binding to a peptide consisting of an amino acid sequence having at least 80% identity to SEQ ID NO:2.

In another embodiment, the present invention is isolated antibody or an antigen-binding fragment thereof that specifically binding to a peptide consisting of an amino acid sequence having at least 80% identity to SEQ ID NO:3.

In another embodiment, the present invention is isolated antibody or an antigen-binding fragment thereof that specifically binding to a peptide consisting of an amino acid sequence having at least 80% identity to SEQ ID NO:4.

In another embodiment, the present invention is an isolated antibody or an antigen binding fragment thereof which specifically binds to a peptide with an amino acid sequence of SEQ ID NO:2 or a fragment thereof.

In another embodiment, the present invention is an isolated antibody or an antigen-binding fragment thereof that specifically binds to a peptide with an amino acid sequence of SEQ ID NO:3 or a fragment thereof.

In a further embodiment, the present invention is an isolated antibody or an antigen-binding fragment thereof that specifically binds to a peptide with an amino acid sequence of SEQ ID NO:4 or a fragment thereof.

In one embodiment, the present invention is a pharmaceutical composition comprising a pharmaceutically acceptable carrier or diluent and an antibody or an antigen binding fragment thereof that specifically binds to a peptide consisting of an amino acid sequence having at least 80% identity to a sequence selected from the group of SEQ ID NO:2, SEQ ID NO:3 and SEQ ID NO:4.

In another embodiment, the present invention is a pharmaceutical composition comprising a pharmaceutically acceptable carrier or diluent and an antibody or an antigen binding fragment thereof that specifically binds to a peptide consisting of SEQ ID NO:2 or a fragment thereof.

In one embodiment, the present invention is a method of treating a subject suffering from an inflammatory condition, comprising administering to said subject an effective amount of an antibody or an antigen binding fragment thereof. The antibody or the antigen binding fragment specifically binds to a peptide consisting of an amino acid sequence having at least 80% identity to a sequence selected from the group of SEQ ID NO:2, SEQ ID NO:3 and SEQ ID NO:4.

In another embodiment, the present invention is a method of treating a subject suffering from an inflammatory condition, comprising administering to said subject an effective amount of an antibody or an antigen binding fragment thereof. The antibody or antigen binding fragment specifically binds to a peptide consisting of an amino acid sequence of SEQ ID NO:2 or a fragment thereof.

Antibodies disclosed herein inhibit pro-inflammatory cytokine production in vitro (Examples 5 and 6) and protects mice against lethality caused by cecal ligation and puncture (CLP) experimental procedure (Example 7).

BRIEF DESCRIPTION OF THE DRAWINGS

FIG. 1 illustrates the amino acid sequence (SEQ ID NO:1) of human α7 subunit of an nicotinic acetylcholine receptor deposited in GenBank under Accession Number P36544.

FIGS. 3A and 3B show lower magnification micrographs. FIG. 3A: Cells were stained with α-bungarotoxin alone. FIG. 3B: 500 μM of nicotine was added prior to the addition of α-bungarotoxin. FIGS. 3C and 3D show higher magnification micrographs to reveal the receptor clusters. FIG. 3C: Focus planes were on the inside layers close to the middle (three lower cells) or close to the surface (upper cell) of cells. FIG. 3D: Focus plane was on the upper surface of the cell.

FIG. 4A shows results of RT-PCR with α7-specific primers, generating a 843 bp α7 band. PCR products were verified by sequencing (data not shown). MAC1 and MAC2: macrophages derived from two unrelated donors. FIG. 3B shows western blots. Cell lysates from PC12 cells or human macrophages (MAC) were incubated with either control Sepharose beads or Sepharose beads conjugated with .alpha.-bungarotoxin. The bound proteins were then analyzed by α7-specific polyclonal and monoclonal antibodies as indicated.

FIG. 7A: Inhibition of TNF release at 40 μg/ml of an antibody. FIG. 7B: Inhibition of IL-8 release at 40 μg/ml of an antibody. FIG. 7C: Inhibition of TNF release at 5 ng/ml of an antibody. FIG. 7D: Inhibition of IL-8 release at 5 ng/ml of an antibody.

FIG. 9A is a plot of percent inhibition of TNFα release as a function of antibody concentration.

FIG. 11A shows immunostaining microphotographs of TNF production in RAW 264.7 cells treated either with Ab1918 (bottom panels) or an irrelevant IgG (top panels) cells following TNF induction by LPS (right panels).

FIG. 11B is a plot illustrating dose-dependent inhibition of TNF production by Ab1918 in RAW 264.7 cells treated with LPS.

FIG. 12A is a plot illustrating dose-dependent inhibition of HMGB1 production by Ab1918 in RAW 264.7 cells treated with LPS.

FIG. 12B shows immunostaining microphotographs of HMGB1 production in RAW 264.7 cells treated either with Ab1918 (bottom panels) or an irrelevant IgG (top panels) cells following HMGB1 induction by LPS (right panels).

FIG. 14A is a bar plot indicating LPS-induced TNF blood serum level in mice following treatment with Ab1918.

FIG. 14B shows immunostaining microphotographs of spleen tissue sections taken from mice treated either with Ab 1918 (bottom right panel) or an irrelevant IgG (bottom left panel) cells following TNF induction by LPS.

FIG. 15A is a bar plot indicating LPS-induced HMGB-1 blood serum level in mice that underwent cecal ligation and puncture, following treatment with Ab1918.

FIG. 15B is a plot comparing survival rates of mice that underwent cecal ligation and puncture, following treatment with either Ab1918 or an irrelevant IgG.

DETAILED DESCRIPTION OF THE INVENTION

Figure 2:
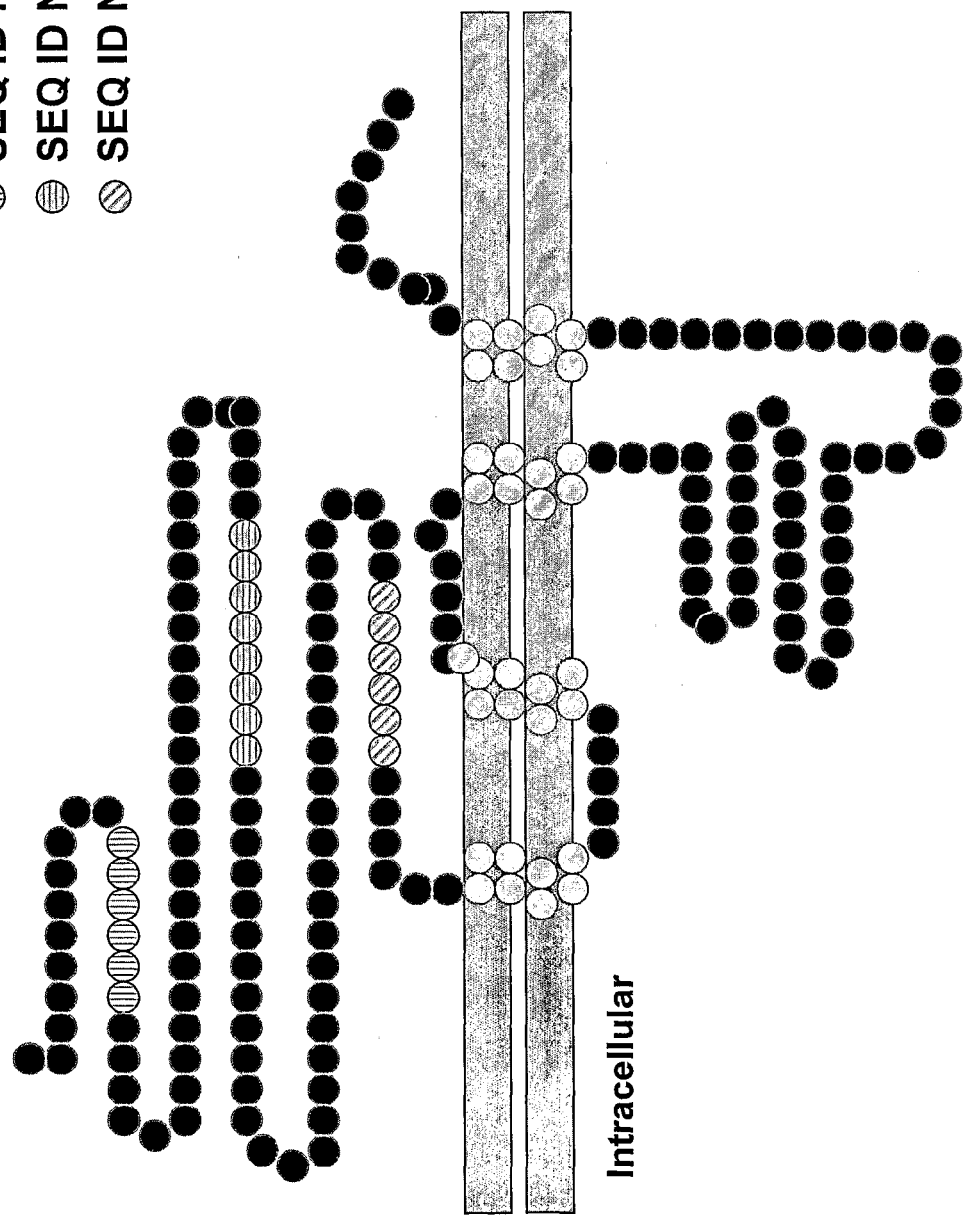
FIG. 2 illustrates peptides (SEQ ID NO:2, SEQ ID NO:3 and SEQ ID NO:4) that were used as immunogens to generate antibodies to the α7 subunit.

The present invention is based on the discovery of specific regions of the α7 subunit, which, upon binding cognate antibodies, stimulate an α7 nicotinic acetylcholine receptor. This stimulation, in turn, inhibits signaling pathways that contribute to inflammatory conditions. Antibodies that have such a stimulatory effect on an α7 nicotinic receptor are α7 receptor agonists (see also below).

Accordingly, in some embodiments, the present invention is a method of treatment of an inflammatory condition in a patient. The method comprises administering to a subject an effective amount of an antibody or an antigen binding fragment thereof, wherein the antibody or its antigen binding fragment stimulates the α7 nicotinic receptor.

As used herein, an "α7 nicotinic receptor" is a nicotinic receptor comprising an α7 subunit. The receptor can comprise only α7 subunits; alternatively the receptor comprises α7 subunit(s) and subunit(s) from other nicotinic receptor subtypes. The receptor can be a homopentamer. Alternatively, the receptor can be a heteropentamer. An "α7 subunit" is intended to include all α7 subunit isoforms and/or variants including, but not limited to, the α7 duplicate nicotinic acetylcholine receptor ("dupα7") described in Villiger et al., Journal of Immunology 126: 86-98 (2002) and Gault et al., Genomics 52:173-85 (1998), the splice variant α7-2 described in US 20040152160 and the promoter variant(s) of the α7 nicotinic receptor described in U.S. Pat. No. 6,875,606. The relevant teachings of these publications are incorporated herein by reference.

As used herein, an "α7 nicotinic receptor agonist" and a "α7 receptor agonist" is a compound (including an antibody) that binds to a receptor comprising an α7 subunit, in vivo or in vitro, inducing the receptor to perform its physiological function. As a result of this induction, a nicotinic receptor agonist inhibits proinflammatory signaling pathways thus alleviating or eliminating inflammation and treating or curing inflammatory conditions.

Antibodies and Antibody-Producing Cells

FIG. 1 shows the amino acid sequence of the human α7 nicotinic receptor subunit (SEQ ID NO:1). Preferably, the antibody of the present invention is a selective agonist of the α7 nicotinic receptor.

The antibody of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments which bind to a mammalian α7 nicotinic receptor. For example, an antibody can be an IgG or antigen-binding fragment of an IgG. Antibody fragments capable of binding to a mammalian α7 nicotinic receptor or fragments thereof, include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain fragment can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising fragments derived from different species, and the like are also encompassed by the present invention and the term "antibody". The various fragments of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for a mammalian (e.g., human) α7 nicotinic receptor can be raised against an appropriate immunogen, such as isolated and/or recombinant human protein of SEQ ID NO:1 or fragments thereof (including synthetic molecules, such as synthetic peptides). Antibodies can also be raised by immunizing a suitable host (e.g., mouse) with cells that express α7 nicotinic receptor, such as macrophages. In addition, cells expressing a recombinant mammalian α7 nicotinic receptor such as transfected cells, can be used as immunogens or in a screen for antibody which binds receptor (see e.g., Chuntharapai et al., J. Immunol., 152: 1783-1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies (see e.g., Jakobovits et al., Proc. Natl. Acad. Sci. USA, 90: 2551-2555 (1993); Jalkobovits et al., Nature, 362: 255-258 (1993); Lonberg et al., U.S. Pat. No. 5,545,806; Surani et al., U.S. Pat. No. 5,545,807; Lonberg et al., WO97/13852).

The invention also relates to a bispecific antibody, or functional fragment thereof (e.g., F(ab')$_2$), which binds to a mammalian α7 nicotinic receptor and at least one other antigen. (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In one embodiment, the antibody or antigen-binding fragment of the invention specifically binds to a fragment of SEQ ID NO:2, SEQ ID NO:3 or SEQ ID NO:4. (FIG. 2 illustrates relative positions of these sequences within an α7 subunit of a human nicotinic receptor.) The fragment can be 5 to 10 amino acids long, 10 to 15 amino acids long or 15 to 19 amino acids long.

Alternatively, the antibody or antigen-binding fragment specifically binds to SEQ ID NO:2, SEQ ID NO:3 or SEQ ID NO:4.

Table 1 lists the above-mentioned amino acid sequences.

TABLE 1

| Amino Acid Sequence | Positions in SEQ ID NO: 1 | SEQ ID NO |
|---|---|---|
| kelvknynplerpvandsqp | 31-50 | SEQ ID NO: 2 |
| wkpdillynsaderfdatfh | 108-127 | SEQ ID NO: 3 |
| krserfyecckepypdvtft | 204-223 | SEQ ID NO: 4 |

In one embodiment, the antibody or antigen-binding fragment binds a functional variant of SEQ ID NO:1 as defined below or a fragment thereof. For example, the antibody or antigen-binding fragment can bind to a peptide that has sequence identity to peptides of SEQ ID NO:2, SEQ ID NO:3 or SEQ ID NO:4. A peptide against which the antibodies will bind can share at least about 80% amino acid sequence similarity with a peptide selected from SEQ ID NO:2, SEQ ID NO:3 or SEQ ID NO:4 or a fragment thereof, preferably at least about 90% amino acid sequence similarity, and more preferably at least about 95% amino acid sequence similarity. Methods that can be used to ascertain sequence similarity are described below.

Antibodies of the invention can be identified by a variety of suitable methods. For example, such an antibody can be identified based upon the ability to compete with any of the above-recited antibody for binding to mammalian α7 nicotinic receptor. In another example, the binding of such an antibody and the binding of an antibody with the same or similar epitopic specificity can be inhibited by a natural peptide or a synthetic peptide. The peptide can comprise five to about fifty amino acids. Preferably, the peptide comprises ten to about twenty one amino acids. In still another example, an antibody with the same or similar epitopic specificity as an antibody as recited above can be identified using chimeric receptors (see e.g., Rucker et al., Cell 87:437-446 (1996)).

In a particular embodiment, the bispecific antibody, or functional fragment thereof has the same or similar epitopic specificity as an antibody that binds to a peptide of SEQ ID NO:2, SEQ ID NO:3 or SEQ ID NO:4 and at least one other antibody.

A nonlimiting example of methods for generating antibodies for the α7 nicotinic receptor is immunizing a suitable laboratory animal with the α7 receptor or a fragment thereof and isolating the antibodies elicited by the immunization which bind α7 subunit. Immunization and isolation procedures are well known to one of ordinary skill in the art.

Selectivity for the α7 nicotinic receptor can be assessed by screening for binding to at least one other nicotinic or cholinergic receptor. Antibodies that are found to be selective agonist for the α7 receptor may be further evaluated for their efficacy in inhibiting cytokine release and/or in treating one or more of the inflammatory diseases described herein, e.g., additional in vitro tests or in vivo tests in animal models.

Antibodies which are agonists can be identified by the procedures disclosed herein, for example, by combining the isolated antibodies with a macrophage that has been stimulated to release proinflammatory cytokine, or any other suitable method for assessing α7 receptor activity. Inhibition of cytokine release is indicative of the agonist activity.

Methods of identifying an agonist antibody against nicotinic receptors in general and α7 receptor in particular will be described below. In a preferred method, the binding activity of an agonist anti-α7 antibody is measured by the activity (current responses) of Xenopus oocytes expressing either the α7 receptor subtype or another receptor subtype (e.g., α4β2) following administration of the agonist. Agonists that result in greater activation of the α7 receptor subtype are determined to be α7 selective agonists.

Functional Assays

A composition comprising a mammalian α7 nicotinic receptor or functional variant thereof can be used in a binding assay to detect and/or identify agents that can bind to the receptor, including antibodies of the invention.

Compositions suitable for use in a binding assay include, for example, cells which naturally express a mammalian α7 nicotinic receptor or functional variant thereof and recombinant cells expressing a mammalian α7 nicotinic receptor or functional variant thereof. Compositions suitable for use in a binding assay also include, membrane preparations which comprise a mammalian α7 nicotinic receptor or functional variant thereof. Such membrane preparations can contain natural (e.g., plasma membrane) or synthetic membranes. Preferably, the membrane preparation is a membrane fraction of a cell that expresses a mammalian α7 nicotinic receptor or a functional variant thereof.

As used herein, "mammalian α7 nicotinic receptor" refers to a naturally occurring or endogenous mammalian protein comprising an α7 subunit of a nicotinic receptor and to proteins having an amino acid sequence which is the same as that of a naturally occurring or endogenous corresponding mammalian α7 subunit protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian α7 subunit (e.g., produced by alternative splicing or other cellular processes), and modified or unmodified forms of the foregoing (e.g., lipidated, glycosylated, unglycosylated). Naturally occurring or endogenous mammalian α7 subunit proteins include wild type proteins such as mature α7 nicotinic receptor, polymorphic or allelic variants and other isoforms which occur naturally in mammals (e.g., humans, non-human primates). Such proteins can be recovered or isolated from a source which naturally produces mammalian α7 subunit, for example.

"Functional variants" of mammalian α7 nicotinic receptor include functional fragments, functional mutant proteins, and/or functional fusion proteins which can be produce using suitable methods (e.g., mutagenesis (e.g., chemical mutagenesis, radiation mutagenesis), recombinant DNA techniques). A "functional variant" is a protein or polypeptide which has at least one function characteristic of a mammalian α7 nicotinic receptor protein as described herein, such as a binding activity, a signaling activity and/or ability to stimulate a cellular response. Preferred functional variants can bind a ligand (i.e., one or more ligands, such as acetylcholine or an antibody of the invention).

Generally, fragments of mammalian α7 nicotinic receptor include those having a deletion (i.e., one or more deletions) of an amino acid (i.e., one or more amino acids) relative to the mature mammalian α7 nicotinic receptor (such as N-terminal, C-terminal or internal deletions). Fragments in which only contiguous amino acids have been deleted or in which non-contiguous amino acids have been deleted relative to mature mammalian α7 nicotinic receptor protein are also envisioned.

Mutant mammalian α7 nicotinic receptors include natural or artificial variants of a mammalian α7 nicotinic receptor differing by the addition, deletion and/or substitution of one or more contiguous or non-contiguous amino acid residues (e.g., receptor chimeras). Such mutations can occur at one or more sites on a protein, for example a conserved region or nonconserved region (compared to other chemokine receptors or G-protein coupled receptors), extracellular region, cytoplasmic region, or transmembrane region.

Fusion proteins encompass polypeptides comprising a mammalian α7 subunit or a variant thereof as a first moiety, linked via a covalent bond (e.g., a peptide bond) to a second moiety not occurring in the mammalian α7 subunit or α7 nicotinic receptor as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human α7 subunit or a fragment thereof. Additional (e.g., third, fourth) moieties can be present as appropriate.

In one embodiment, a functional variant of mammalian α7 nicotinic receptor subunit (e.g., a ligand binding variant) shares at least about 80% amino acid sequence similarity with said mammalian α7 subunit, preferably at least about 90% amino acid sequence similarity, and more preferably at least about 95% amino acid sequence similarity with said mammalian α7 subunit (e.g., a human α7 subunit (e.g., SEQ ID NO:1)). In another embodiment, a functional fusion protein comprises a first moiety which shares at least about 85% sequence similarity with a mammalian α7 subunit, preferably at least about 90% sequence similarity, and more preferably at least about 95% sequence similarity with a mammalian α7 subunit. In another embodiment, a functional mammalian α7 subunit or functional variant of a mammalian α7 subunit shares at least about 80% amino acid sequence similarity, preferably at least about 90% amino acid sequence similarity, and more preferably at least about 95% amino acid sequence with a naturally occurring human α7 subunit.

Amino acid sequence similarity can be determined using a suitable sequence alignment algorithm, such as the LASER-GENE system (sequence assembly and alignment software; DNASTAR, Inc., Madison, Wis.), using the Clustal method with the PAM 250 residue weight table, a gap penalty of 10, a gap length penalty of 10 and default parameters (pairwise alignment parameters: ktuple=1, gap penalty=3, window-4 and diagonals saved=5).

In another embodiment, a functional variant is encoded by a nucleic acid sequence which is different from the naturally-occurring nucleic acid sequence, but which, due to the degeneracy of the genetic code, encodes mammalian α7 subunit or a fragment thereof.

In one embodiment, the method of detecting or identifying an antibody that binds to a mammalian α7 nicotinic receptor is a competitive binding assay in which the ability of a test agent (e.g. an antibody) to inhibit the binding of a reference agent (e.g., a ligand or another antibody of known specificity) is assessed. For example, the reference agent can be labeled with a suitable label as described herein, and the amount of labeled reference agent required to saturate the α7 nicotinic receptor present in the assay can be determined. A saturating amount of labeled reference agent and various amounts of a test agent can be contacted with a composition comprising a mammalian α7 nicotinic receptor or functional variant thereof under conditions suitable for binding and complex formation determined.

The formation of a complex between either the reference or a test agent and the α7 nicotinic receptor or functional variant thereof or fragments thereof including immunogenic peptides as described above can be detected or measured directly or indirectly using suitable methods. For example, the agent can be labeled with a suitable label and the formation of a complex can be determined by detection of the label. The specificity of the complex can be determined using a suitable control such as unlabeled agent or label alone. Labels suitable for use in detection of a complex between an agent and a mammalian α7 nicotinic receptor or functional variant thereof include, for example, a radioisotope, an epitope, an affinity label (e.g., biotin, avidin), a spin label, an enzyme, a fluorescent group or a chemiluminescent group.

With respect to a competitive binding assays used to determine the ability of a test agent such as an antibody to bind an α7 nicotinic receptor, such ability can be reported as the concentration of test agent required for 50% inhibition ($IC_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian α7 subunit or a functional variant thereof, for example, a ligand of α7 subunit or an antibody. Preferred reference agents are antibodies having a known specificity against the fragments of the α7 subunit of a human nicotinic receptor (SEQ ID NO:1) selected from the group of SEQ ID NO:2, SEQ ID NO:3 and SEQ ID NO:4.

Validation of efficacy of an Ab of the invention can be performed by determining whether an antibody inhibits release of a proinflammatory cytokine from a mammalian cell.

These methods preferably involve treating the mammalian cell with an antibody along with an agent that stimulates a proinflammatory cytokine cascade. A preferred agent is bacterial lipopolysaccharide (LPS). The compound can be administered to the mammalian cell either before the agent, at the same time as the agent, or after the agent. Preferably, the compound is administered before the agent. See, e.g., U.S. Pat. No. 6,610,713, the relevant teachings of which are incorporated herein by reference.

For these methods, the cell can be any cell that can be induced to produce a proinflammatory cytokine. In preferred embodiments, the cell is an immune cell, for example macrophages, monocytes, or neutrophils. In the most preferred embodiments, the cell is a macrophage.

The proinflammatory cytokine to be measured for inhibition can be any proinflammatory cytokine that can be induced to be released from the cell. In preferred embodiments, the cytokine is TNF.

Evaluation of the inhibition of cytokine production can be by any means known, including quantitation of the cytokine (e.g., with ELISA), or by bioassay, (e.g. determining whether proinflammatory cytokine activity is reduced), or by measurement of the proinflammatory cytokine mRNA. The skilled artisan could utilize any of these assays without undue experimentation. See also U.S. Pat. No. 6,610,713, the relevant teachings of which are incorporated herein by reference, for examples of several assays useful in this regard.

These methods can be performed in vivo, where an animal, e.g., a rat, is treated with the compound along with an agent that stimulates a proinflammatory cytokine cascade, and the effect of the agent on induction of the proinflammatory cytokine cascade is measured, e.g., by measuring serum TNF levels. However, due to the relative ease of doing these types of assays with cells culture rather than with whole animals, the methods are preferably performed in vitro, for example using macrophage cultures.

In other embodiments, the invention is directed to methods for determining whether an antibody has the ability to inhibit inflammation. In some aspects, these methods comprise determining whether an antibody is an agonist of the α7 nicotinic receptor. Preferably the methods further comprise determining whether an antibody is selective for α7 by testing the antibody for its ability to activate at least one other nicotinic receptor. These determinations can be made as previously described, e.g., by determining whether the antibody inhibits release of a proinflammatory cytokine from a mammalian cell, preferably a macrophage.

Methods of Therapy

The present invention is directed toward treating cytokine-mediated inflammatory conditions where the level of cytokine release can be reduced by α7 receptor activation. In preferred embodiments, the condition is one where the inflammatory cytokine cascade is affected through release of proinflammatory cytokines from a macrophage. The condition can be one where the inflammatory cytokine cascade causes a systemic reaction, such as with septic shock. Alternatively, the condition can be mediated by a localized inflammatory cytokine cascade, as in rheumatoid arthritis.

Nonlimiting examples of conditions which can be usefully treated using the present invention include appendicitis, peptic, gastric or duodenal ulcers, peritonitis, pancreatitis, acute or ischemic colitis, diverticulitis, epiglottitis, achalasia, cholangitis, cholecystitis, hepatitis, inflammatory bowel disease (including, for example, Crohn's disease and ulcerative colitis), enteritis, Whipple's disease, asthma, chronic obstructive pulmonary disease, ileus (including, for example, post-operative ileus), allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome, or Hodgkins disease.

In one embodiment, the condition is selected from appendicitis, peptic, gastric and duodenal ulcers, peritonitis, pancreatitis, hepatitis, asthma, allergy, anaphylactic shock, organ necrosis, hay fever, sepsis, septicemia, endotoxic shock, cachexia, septic abortion, disseminated bacteremia, burns, coeliac disease, congestive heart failure, adult respiratory distress syndrome, chronic obstructive pulmonary disease, rheumatoid arthritis, systemic lupus erythematosis, myocardial ischemia, cerebral infarction, cerebral embolism, spinal cord injury, paralysis, allograft rejection or graft-versus-host disease.

In an alternative embodiment, the condition is selected from the group consisting of peritonitis, pancreatitis, sepsis, endotoxic shock, adult respiratory distress syndrome, chronic obstructive pulmonary disease, rheumatoid arthritis, systemic lupus erythematosis, Crohn's disease, ulcerative colitis, ileus, Alzheimer's disease, burns, myocardial ischemia, allograft rejection, asthma, graft-versus-host-disease, congestive heart failure and cystic fibrosis.

These conditions are preferably treated with the antibodies disclosed herein or a combination of an antibody disclosed herein and one or more additional agonists of an α7 nicotinic receptor. Suitable additional agonists are disclosed, for example, in a co-pending U.S. patent application Ser. No. 10/729,427. The relevant teachings of U.S. patent application Ser. No. 10/729,427 are incorporated herein by reference.

Modes of Administration

The route of administration of the α7 receptor agonist depends on the condition to be treated. For example, intravenous injection may be preferred for treatment of a systemic disorder such as septic shock, and oral administration may be preferred to treat a gastrointestinal disorder such as a gastric ulcer.

According to the method, one or more antibodies of the present invention can be administered to the subject by an appropriate route, either alone or in combination with another drug. An effective amount of an agent (i.e. a α7 receptor agonist antibody or antigen-binding fragment thereof) is administered. An "effective amount" is an amount sufficient to achieve the desired therapeutic or prophylactic effect, under the conditions of administration, such as an amount sufficient for inhibition of an inflammatory response and alleviating or curing an inflammatory condition. The agents can be administered in a single dose or multiple doses. The dosage can be determined by methods known in the art and is dependent, for example, upon the particular agent chosen, the subject's age, sensitivity and tolerance to drugs, and overall well-being. Suitable dosages for antibodies can be from about 0.01 mg/kg to about 100 mg/kg body weight per treatment.

A variety of routes of administration are possible including, for example, oral, dietary, topical, transdermal, rectal, parenteral (e.g., intravenous, intraarterial, intramuscular, subcutaneous injection, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (α7 receptor agonist antibody or an antigen-binding fragment thereof) chosen, and the particular condition (e.g., disease) being treated. Intravenous, oral or parenteral administration are preferred.

The agent can be administered as a neutral compound or as a pharmaceutically acceptable salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

As used herein, a "pharmaceutically acceptable salt" of a disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The agent can be administered to the individual as part of a pharmaceutical composition for modulation of nicotinic receptor function comprising an inhibitor of such function and a pharmaceutically acceptable carrier.

As used herein, a "pharmaceutical composition" is a formulation comprising the disclosed antibodies and a pharmaceutically acceptable diluent or carrier, in a form suitable for administration to a subject. Suitable pharmaceutically acceptable carriers include inert solid fillers or diluents and sterile aqueous or organic solutions. Formulation will vary according to the route of administration selected (e.g., solution, emulsion, capsule). Suitable pharmaceutical carriers can contain inert ingredients which do not interact with the promoter (agonist) or inhibitor (antagonist) of nicotinic receptor function. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration.

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the Example.

EXEMPLIFICATION

Example 1

Macrophages Express Nicotinic Receptor α7 Subunit

Example Summary

We previously reported that the α7 subunit of a nicotinic receptor is required for acetylcholine-mediated inhibition of macrophage TNF release. (See co-pending U.S. patent application Ser. No. 10/729,427.) As summarized below, α-bungarotoxin bound to discrete receptor clusters expressed on the surface of primary human macrophages and immunoblotting of proteins isolated by adherence to α-bungarotoxin-conjugated beads with α7-specific antibodies thus confirming the identity of the α-bungarotoxin-binding receptor subunit as the α7 subunit.

Results and Discussion

Figure 3:
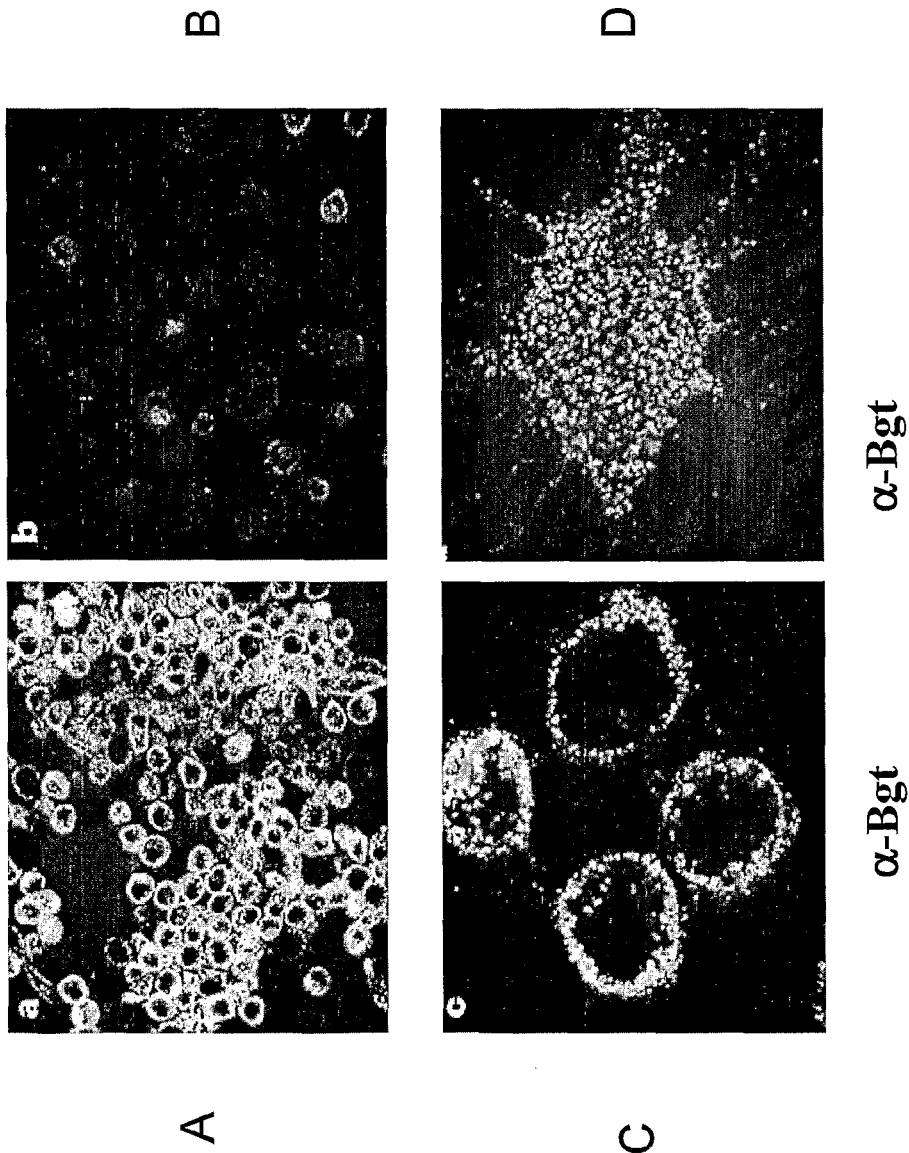
FIGS. 3A-D are fluorescent micrographs establishing that α-bungarotoxin-binding nicotinic receptors are clustered on the surface of macrophages. Primary human macrophages were stained with FITC-labeled α-bungarotoxin (α-bgt, 1.5 μg/ml) and viewed with a fluorescent confocal microscope.

Primary human macrophages were labeled with FITC-α-bungarotoxin, a peptide antagonist that binds to a subset of acetylcholine receptors. Strong binding of α-bungarotoxin was observed on the macrophage surface (FIG. 3A). Nicotine pretreatment markedly reduced the intensity of binding (FIG. 3B). At neuro-muscular junctions and the neuronal synapses, nicotinic receptors form receptor aggregates or clusters that facilitate fast signal transmission. Discrete clusters of α-bungarotoxin binding can be clearly observed under higher magnification on the surface of macrophages, especially concentrated on the surface of the cell body (FIG. 3C, D).

To date, α1, α7 and α9 are the α-bungarotoxin-binding nicotinic receptor subunits known in human cells (Lindstrom, J. M. Nicotinic acetylcholine receptors. In "Hand Book Of Receptors And Channels: Ligand- And Voltage-Gated Ion Channels." Edited by R. Alan North. CRC Press, Inc. (1995); Leonard, S. and Bertrand, D. Neuronal nicotinic receptors: from structure to function. Nicotine & Tobacco Res. 3:203-223 (2001)). α1 together with β1, δ and either ε (adult) or γ (fetal) subunits, forms heteropentameric nicotinic receptors that regulate muscle contraction; α7 and α9 can each form homopentameric nicotinic receptors. To determine if these receptor subunits are expressed in macrophages, we isolated RNA from primary human macrophages differentiated in vitro from peripheral blood mononuclear cells (PBMC) and performed RT-PCR analyses. To increase the sensitivity and specificity of the experiments, we conducted two rounds of PCR after reverse transcription, using nested primers specific to each subunit. The identities of the PCR products were confirmed by sequencing. The expression of α1, α10, (data not shown) and α7 (FIG. 4A) mRNA was detected in human macrophages derived from unrelated blood donors. The same RT-PCR strategy did not detect the expression of α9 subunit mRNA in macrophages (data not shown).

Figure 4:
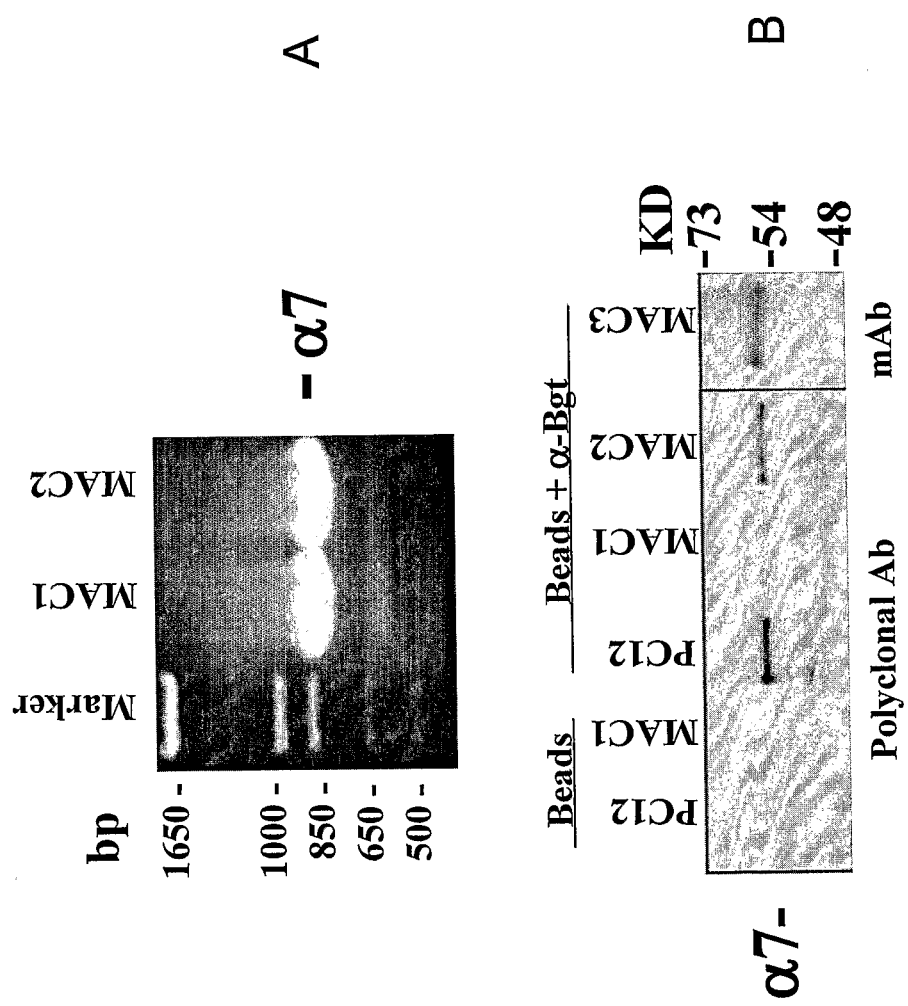
FIG. 4 presents photographs of gels and western blots showing the mRNA and protein expression of α7 and α1 nicotinic receptors in primary human macrophages.

The protein expression of α1 and α7 subunits was next examined by western blotting. The α7 specific antibody recognized a clear band with an apparent molecular weight of about 55 kD (similar to the molecular weight for α7 protein reported by Peng, X. et al. Human α7 acetylcholine receptor: cloning of the α7 subunit from the SH-SY5Y cell line and determination of pharmacological properties of native receptors and functional α7 homomers expressed in *Xenopus oocytes*. Mol. Pharmacol. 45:546-554 (1994)) from both differentiated primary macrophages and from undifferentiated PBMCs (data not shown). α1 protein expression was downregulated to undetectable levels during in vitro differentiation of PBMC to macrophages (data not shown). The δ subunit, a necessary component of the α1 heteropentameric nicotinic acetylcholine receptor, could not be detected by this nested RT-PCR strategy (data not shown). To confirm that the positive signals in macrophages represented α7 nicotinic receptor that binds α-bungarotoxin, we used α-bungarotoxin-conjugated beads to pull-down proteins prepared from either human macrophages or PC12 cells (rat pheochromocytoma cells, which have been shown to express α7 homopentamer). Retained proteins were analyzed by western blotting using polyclonal or monoclonal α7 specific antibodies that recognized both human and rat α7 protein (the human and rat α7 proteins contain the same number of amino acids and are 94% identical). The results clearly showed that the human macrophages express α-bungarotoxin-binding α7 protein with apparent molecular weight that is similar to α7 subunit in PC12 cells (FIG. 4B). The identity of the macrophage α7 subunit was confirmed by cloning of the full-length macrophage-expressed α7 by RT-PCR methods. The full-length nicotinic acetylcholine α7 subunit in macrophages contains exons 1 to 10, identical to the nicotinic acetylcholine α7 subunit expressed in neurons (Gault, J. et al. Genomic organization and partial duplication of the human α7 neuronal nicotinic acetylcholine receptor gene (CHRNA7). Genomics 52:173-185 (1998)). Together, these data identify the nicotinic acetylcholine α7 subunit as the α-bungarotoxin-binding receptor expressed on the surface of human macrophages.

Example 2

Preparation of Rabbit Polyclonal Antibody Against α7 Nicotinic Receptors

Polyclonal antibodies against the extracellular domain and specific peptides of the α7 nicotinic receptor were generated in rabbits according to the 118 day protocol for Custom Polyclonal Antibody Production (Covance Research Products, Inc., Denver, Pa.). Briefly, the peptides were diluted with sterile saline and combined with an equal volume of Freund's Complete Adjuvant. 0.125 mg antigen (antigen includes the peptides described below and GST N-terminal extracellular domain) in Freund's Incomplete Adjuvant were injected six times subcutaneously into rabbits at weeks 3, 6, 9, 12 and 15 after pre-bleed at Day 0. Blood was collected from the ear vein 10 days after injection at weeks 9, 12 and 15. Sera from the rabbits were assayed for titer by Western blotting. IgG was purified from anti-α7 antiserum using Protein A agarose according to manufacturer's instructions [Sigma, St. Louis, Mo.].

The peptide KELVINYNPLERPVANDSOP (SEQ ID NO: 2, corresponding to amino acids 31-50 of SEQ ID NO:1) was injected into two different rabbits in order to generate antibodies 1918 and 1920. The peptide WKPDILLYNSADERFDATFH (SEQ ID NO: 3, corresponding to amino acids 108-127 of SEQ ID NO:1) was injected in two different rabbits in order to generate antibodies 1921 and 1922. The peptide KRSERFYECCKEPYPDYTYT (SEQ ID NO:4, corresponding to amino acids 204-223 of SEQ ID NO:1) was injected into two different rabbits in order to generate antibodies 1923 and 1924. Amino acids 1-227 (corresponding to the extracellular domain of α7), was expressed as a GST-fusion protein in *E. coli*. The GST-fusion protein was purified and was injected into ten different rabbits to generate antibodies 1973 to 1982.

Figure 5:
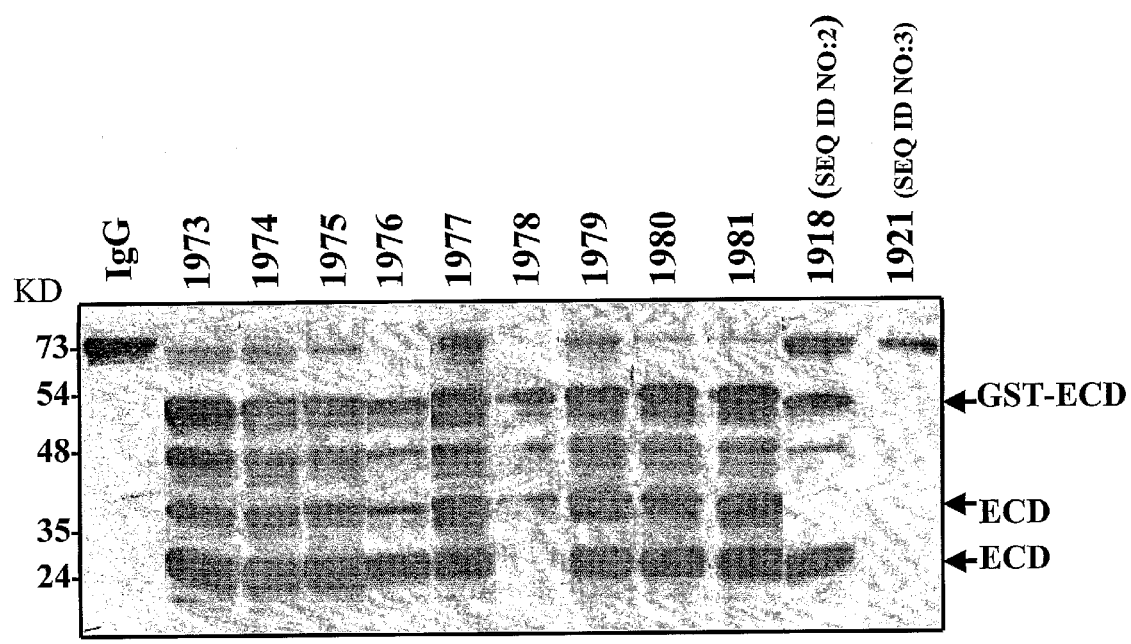
FIG. 5 is a photograph of western blot showing binding specificities of a number of rabbit polyclonal antibodies raised against various fragments of SEQ ID NO:1. Antibodies 1973-1981 were raised against various fragments of SEQ ID NO:1 spanning positions 23 through 250. Antibody 1918 was raised against a peptide of SEQ ID NO:2; antibody 1921 was raised against a peptide of SEQ ID NO:3.

Results are presented in FIG. 5, which shows a photograph of a western blot showing binding specificities of a number of rabbit polyclonal antibodies raised against various fragments of SEQ ID NO:1. Antibodies 1973-1981 were raised against various fragments of SEQ ID NO:1 spanning positions 23 through 250. Antibody 1918 was raised against a peptide of SEQ ID NO:2; antibody 1921 was raised against a peptide of SEQ ID NO:3.

Example 3

Expression of α7 Subunit of a Nicotinic Receptor in Cell Lines

The expression of the α7 subunit in cell lines and primary human macrophages was screened by Western blot using antibody 1918.

Murine macrophage-like RAW 264.7, Jurkat cell, Hela cell, U937cell and PC12 cell were obtained from ATCC (American Type Culture Collection, Rockville, Md.). Cells were cultured in RPMI 1640 or DMEM medium, supplemented with 10% heat-inactivated FBS, 2 mM glutamine, 1× penicillin and streptomycin in a humidified incubator with 5% $CO_2$ and 95% room air. Primary human macrophages were isolated from blood of three donors.

Cell lysates were prepared by incubating the cells with cold lysis buffer (1% Brij 97, 50 mM Tris, pH7.5, 150 mM sodium chloride, 1 mM EDTA, 1 mg/ml each of leupeptin and pepstatin, 1 mM PMSF and 10 mM sodium fluoride). Each cell lysate ($2 \times 10^5$ cell equivalents) were subjected to SDS-PAGE and immunoblotted with antibody 1918. The signal was detected using an ECL kit as instructed by the manufacturer (Amersham Life Science, Inc., Arlington Heights, Ill.).

Figure 6:
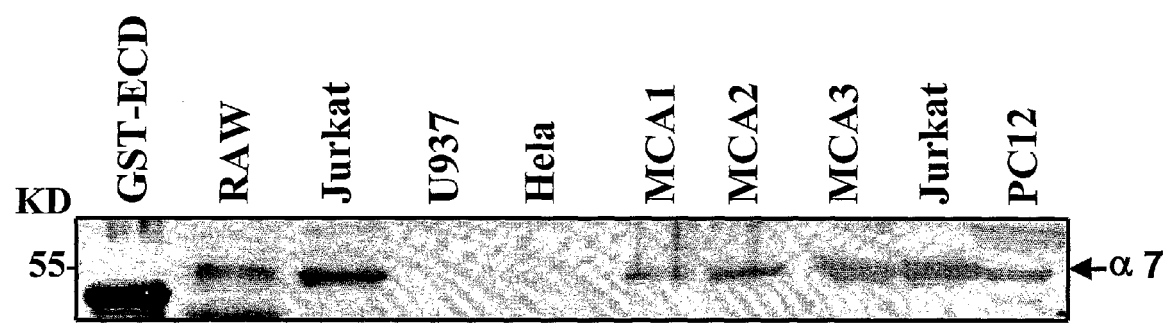
FIG. 6 is a photograph of a western blot showing expression of the α7 subunit in the indicated cell lines. The primary antibody used was the antibody 1918 raised against a peptide having the sequence of SEQ ID NO:2.
Figure 7A:
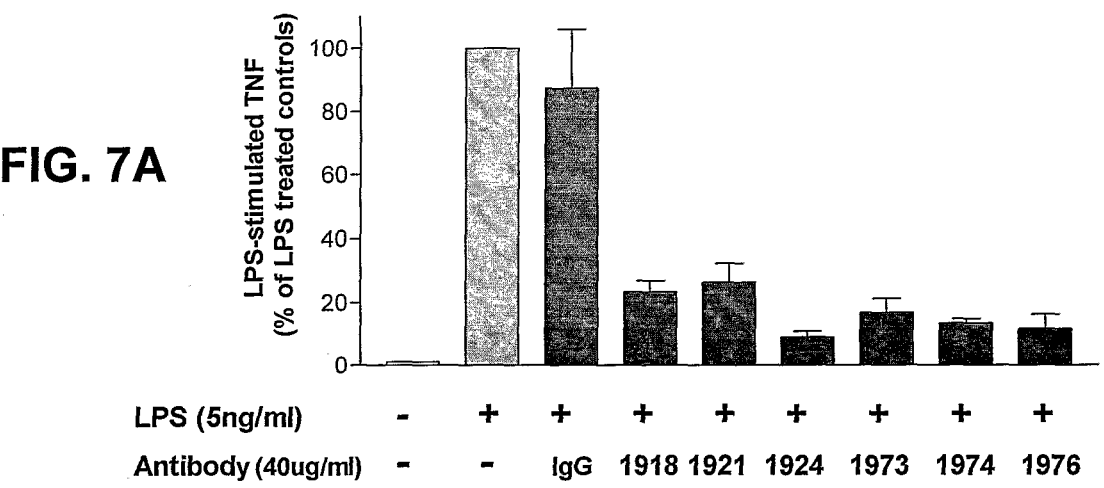
FIGS. 7A-D are bar plot showing activities of selected antibodies of the present invention at different concentrations. Activity is expressed as percent inhibition of a cytokine release from LPS-stimulated primary human macrophages.
Figure 7B:
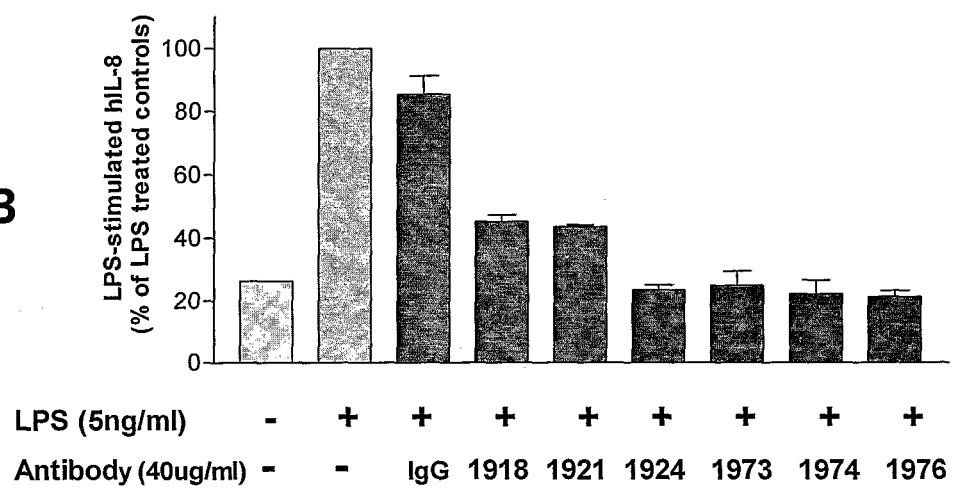
Figure 7C:
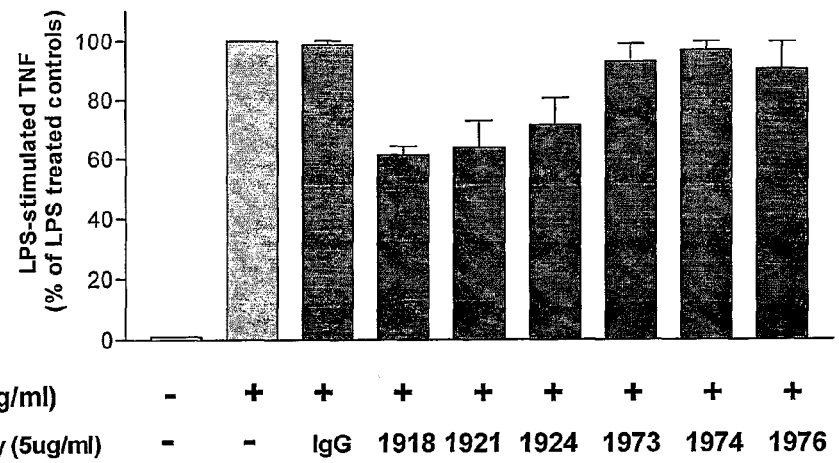
Figure 7D:
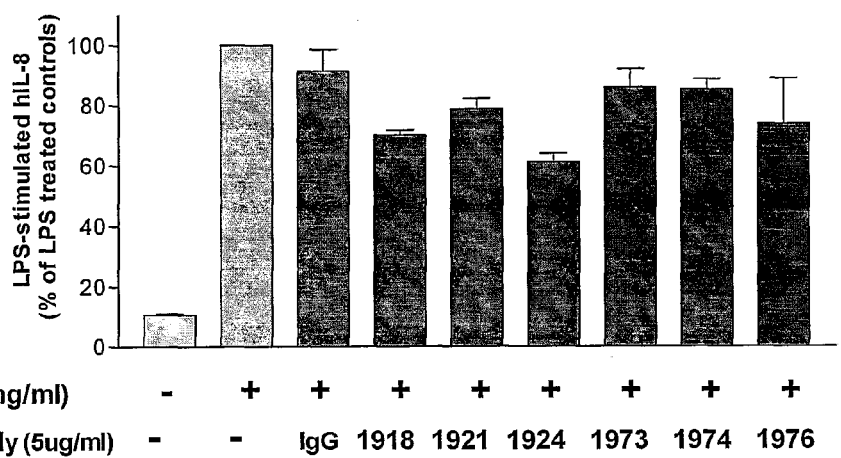

The results of this experiment are presented in FIG. 6.

Example 4

Antibodies Raised Against a Fragment of α7 Subunit of a Nicotinic Receptor Comprising SEQ ID NO:2 Inhibit TNFα and IL-8 Production in LPS-Stimulated Macrophages Human macrophage cultures were prepared as follows. Buffy coats were collected from the blood of healthy individual donors. Primary blood mononuclear cells were isolated by density-gradient centrifugation through Ficoll/Hypaque (Pharmacia, N.J.), suspended ($8 \times 10^6$ cells/ml) in RPMI 1640 medium supplemented with 10% heat inactivated human serum (Gemini Bio-Products, Inc., Calabasas, Calif.), and seeded in flasks (PRIMARIA; Beckton and Dickinson Labware, Franklin Lakes, N.J.). After incubation for 2 hours at 37° C., adherent cells were washed extensively, treated briefly with 10 mM EDTA, detached, resuspended ($10^6$ cells/ml) in RPMI medium (10% human serum), supplemented with human macrophage colony stimulating factor (MCSF; Sigma Chemical Co., St. Louis, Mo.; 2 ng/ml), and seeded onto 24-well tissue culture plates (PRIMARIA; Falcon) ($10^6$ cells/well). Cells were allowed to differentiate for 7 days in the presence of mCSF. On day 7 the cells were washed 3 times with 1× Dulbecco's phosphate buffered saline (PBS, Gibco-BRL, Life Technologies, Rockville, Md.), fresh medium devoid of mCSF was added, and experiments performed as indicated.

Primary human macrophage cultures were established by incubating human peripheral blood mononuclear cells in the presence of macrophage colony stimulating factor (MCSF; Sigma Chemical Co., St. Louis, Mo.). These cells were used in experiments to determine the effects of the antibodies of the present invention on TNFα and IL-8 levels in macrophage cultures conditioned by exposure to LPS for 4 hours.

In these experiments, antibodies 1918 (raised against the peptide of SEQ ID NO:2), 1921 (raised against the peptide of SEQ ID NO:3) as well as antibodies 1924, 1973, 1974 and 1976 (raised against various fragments of SEQ ID NO:1) as well as control (irrelevant IgG antibody) was added to human macrophage cultures at the concentrations of either 40 µg/ml or 5 µg/ml as indicated for thirty minutes (FIGS. 7A-D). LPS was added thirty minutes later (5 ng/ml), and conditioned supernatants collected after 2.5 hours of stimulation for subsequent analysis by enzyme-linked immunosorbent assay (ELISA). All the experimental conditions were performed in triplicate. Data from nine separate macrophage preparations are shown as Mean±SEM; n=9.

As can be seen from FIGS. 7A-D, all tested antibodies showed inhibitory activity (i.e. agonist activity with respect to the acetylcholine receptor) activity at 40 µg/ml when compared to an irrelevant antibody control. Even at 5 ng/ml, antibodies 1918, 1921 and 1924 showed significant inhibition of TNFα and IL-8 release compared to the control.

Example 5

Antibodies Raised Against a Fragment of α7 Subunit of a Nicotinic Receptor Comprising SEQ ID NO:2 Suppress TNF Release from LPS-Stimulated RAW Cells Murine RAW 264.7 macrophage-like cells (American Type Tissue Culture Collection, Rockville, Md., USA) were grown under DMEM supplemented with 10% fetal bovine serum, penicillin and streptomycin. The cells were seeded in 24-well tissue culture plates in Opti-MEM 1 medium and used at 90% confluence. As indicated, cells were treated with LPS (5 ng/ml) for 2.5 hours. As indicated, the cells were pre-treated with 40 ug/ml of antibody 1918 (raised against the peptide of SEQ ID NO:2) for thirty minutes. Supernatants were collected and TNF concentration was measured by mouse ELISA kit (R&D Systems Inc., Minneapolis, Minn.).

Figure 8:
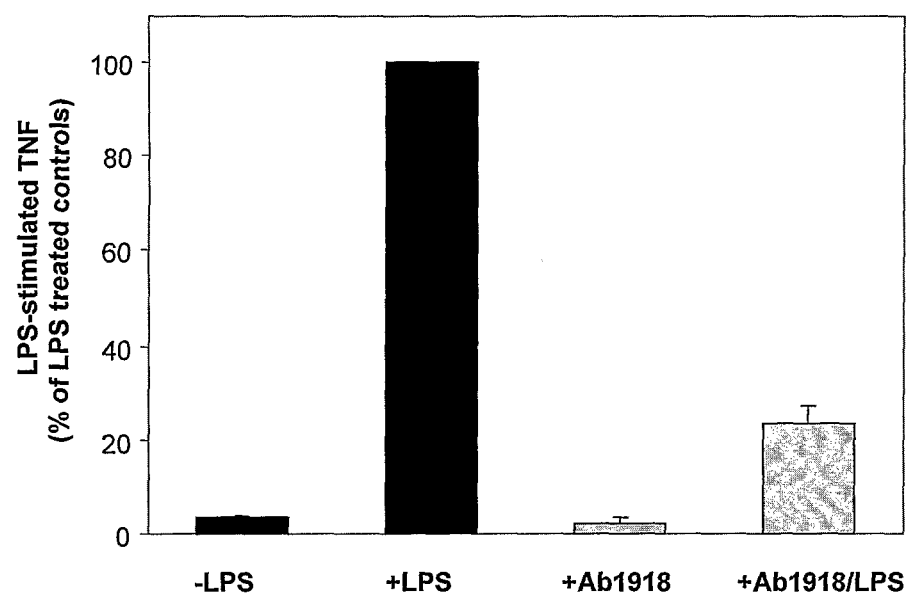
FIG. 8 is a bar plot showing α7 agonist activities of the 1918 antibody raised against a fragment of the human α7 subunit of a nicotinic receptor (SEQ ID NO:1) encompassed in SEQ ID NO:2. Activity is expressed as percent inhibition of TNF release from LPS-stimulated RAW cells.

The results are shown in FIG. 8, which clearly shows that antibody 1918 inhibited TNFα production in RAW cells.

Example 6

Antibodies Raised Against a Fragment of U7 Subunit of a Nicotinic Receptor Comprising SEQ ID NO:2 Suppress TNFα and HMGB-1 Release from LPS-Stimulated Macrophages in a Dose-Dependent Manner Macrophages were grown as described in Example 4 above.

In the experiments in which the inhibitory effect of antibody 1918 (raised against the peptide of SEQ ID NO:2) on TNFα release was determined, the antibody was added at 0, 2.5, 5, 10, 20, 40, 80, and 160 µg/ml. In the experiments in which the inhibitory effect of antibody 1918 on HMGB-1 release was determined, the antibody was added at 0, 10, 50 and 100 ng/ml.

Thirty minutes after the addition of antibody 1918, the cultures were treated with LPS at a concentration of 5.0 ng/ml. Culture medium was collected after 18 hours. The culture medium was concentrated with a Centricon™ 10 filter. TNFα levels was analyzed using a human ELISA kit (R&D Systems Inc., Minneapolis, Minn.). HMGB-1 level was analyzed by western blot using anti-HMGB1 polyclonal antisera as described in U.S. Pat. No. 6,303,321, the relevant teachings of which are incorporated herein by reference. The results of the TNFα inhibition are presented in FIG. 9A as percent stimulation of LPS treatment alone. The results of HMGB-1 inhibition are presented in FIG. 9B as the progressive decrease in band intensity.

Figure 9A:
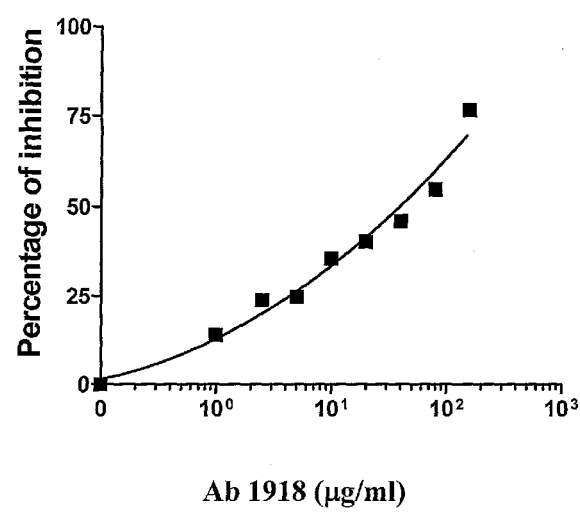
FIGS. 9A and B illustrate dose dependence of inhibition of TNFα (FIG. 9A) and HMGB-1 (FIG. 9B) release from macrophages by α7 antibody 1918, raised against a fragment of the human α7 subunit of a nicotinic receptor (SEQ ID NO:1) encompassed by SEQ ID NO:2.
Figure 9B:
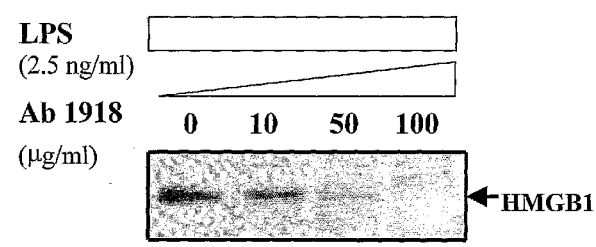
FIG. 9B is a photograph of a western blot showing the dose-dependent reduction in intensity of the band corresponding to HMGB-1.

FIGS. 9A and 9B clearly shows that antibody 1918 inhibited release of TNFα and HMGB-1 in a dose-dependent manner.

Example 7

Agonist Antibody Raised Against a Peptide of SEQ ID NO:2 Protects Mice Against Lethality Caused by CLP Cecal Ligation and Puncture (CLP) was performed as described in Fink and Heard, J. of Surg. Res. 49:186-196 (1990), Wichman et al., Crit. Care Med. 26:2078-2086 (1998) and Remick et al., Shock 4:89-95 (1995). Briefly, Balb/c mice were anesthetized with 75 mg/kg Ketamine (Fort Dodge, Fort Dodge, Iowa) and 20 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, without direct extrusion of stool. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered subcutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate.

Figure 10:
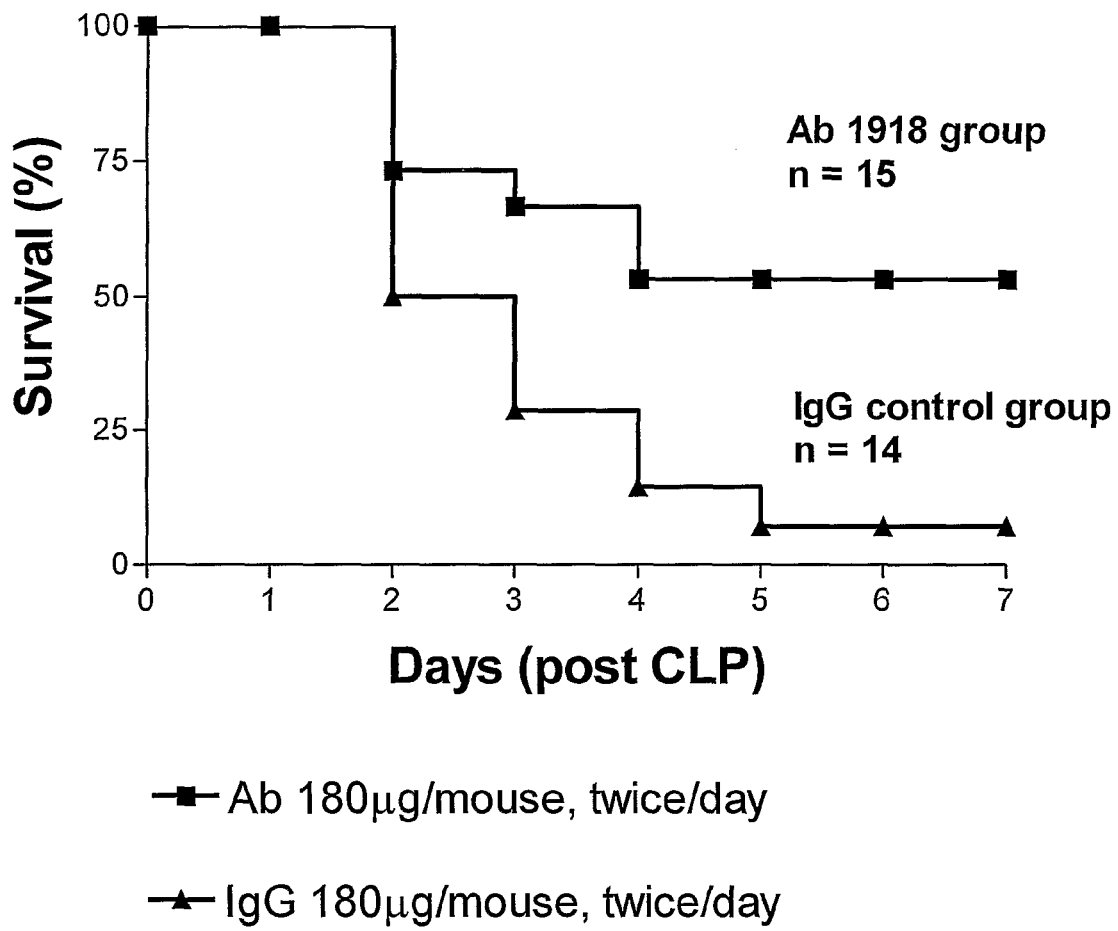
FIG. 10 is a plot showing percent survival of mice subjected to cecal ligation and puncture (CLP) procedure as a function of a number of days post CLP. Two groups of mice are shown: the group treated with antibody 1918 (raised against a peptide of SEQ ID NO:2) and the group treated by an irrelevant IgG (control).

Mice were treated with either antibody 1918 (raised against a peptide of SEQ ID NO:2) at 180 mg/mouse twice daily or a control IgG antibody at 180 mg/mouse twice daily. The agonist and the control antibodies were administered intraperitoneally (i.p.) twice a day for the indicated number of days. Mortality was monitored daily for fourteen days after surgery. The results are presented in FIG. 10, which shows the percentage of surviving animals following treatment with either agonist 1918 antibody, or irrelevant control. As shown in FIG. 10, at 7 days post-CLP, about 10% of mice treated with IgG control antibody survived whereas about 50% of mice treated with antibody 1918 survived. These results demonstrate that agonist antibodies raised against a specific region of the α7 subunit significantly improved survival in the murine CLP model of sepsis.

Example 8

Antibody 1918 Inhibits Endotoxin-Induced TNF Release in RAW 264.7 Cell

Figure 11A:
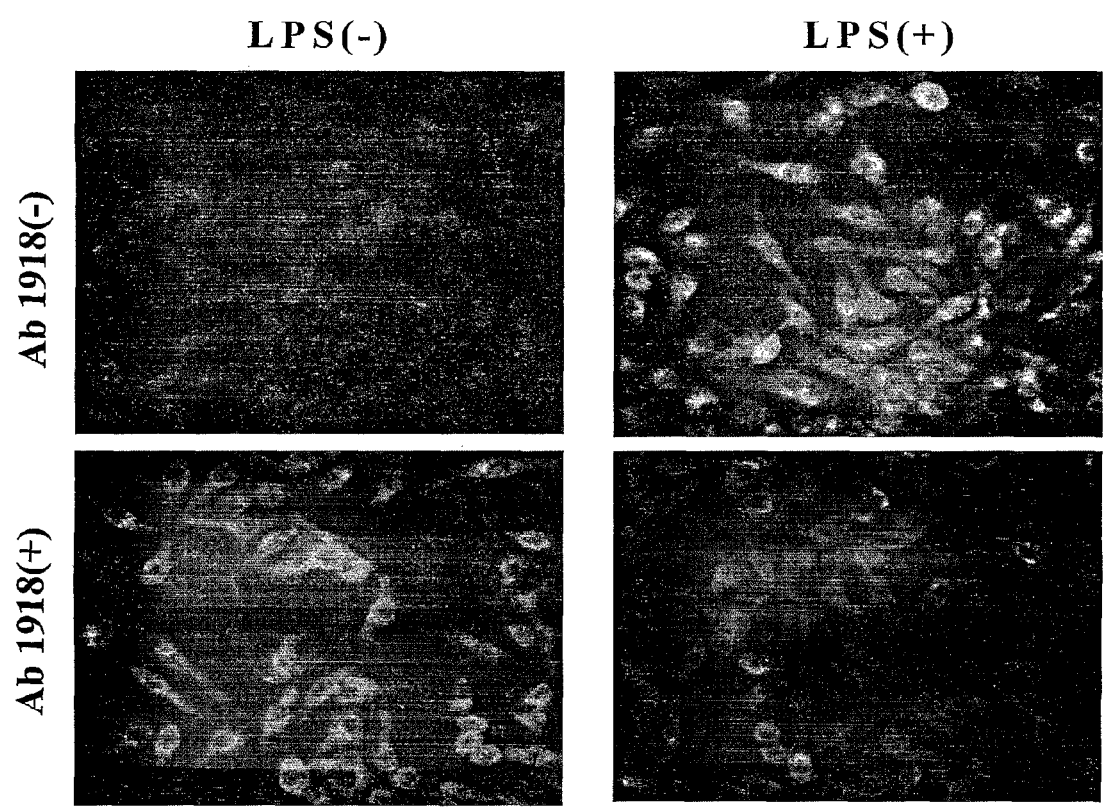
FIGS. 11A-B shows inhibition of TNF levels in RAW 264.7 cells in micrograph and plot formats.

RAW cells were exposed to LPS in the presence IgG or Ab1918 (20 mg/ml). TNF in the cell was analyzed 1.5 hours later by immunostaining with anti-TNF antibodies. The results are presented in FIG. 11A. As can be seen from the diminished fluorescence (the lower right panel), treatment with Ab1918 significantly reduces the level of TNF induced by LPS treatment.

Figure 11B:
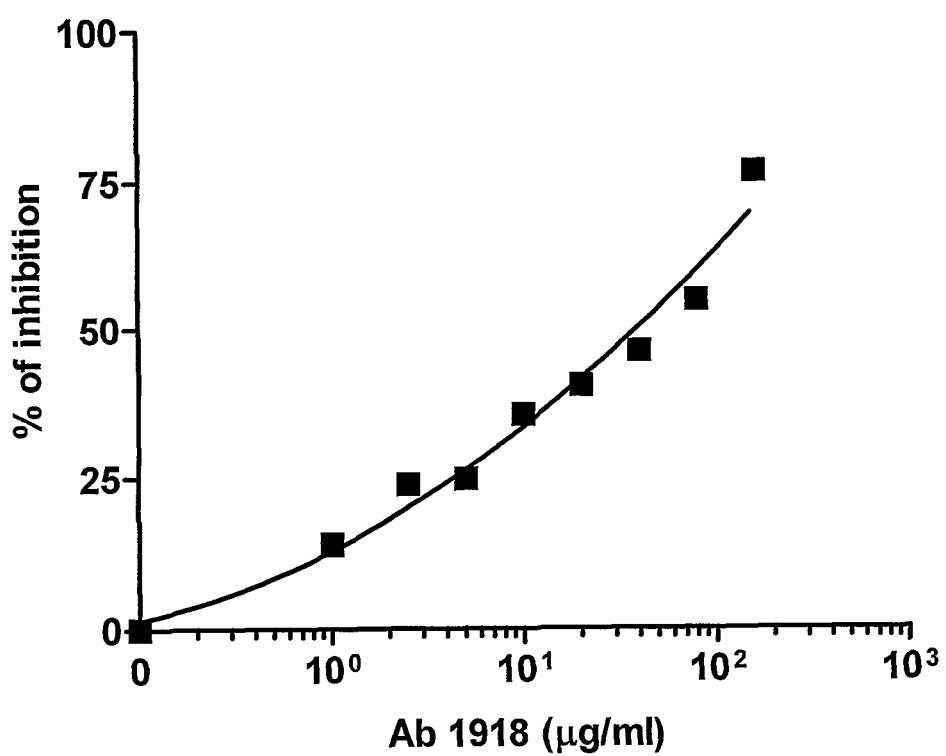

FIG. 11B demonstrates dose-dependent inhibition of TNF release by Ab1918. Primary human macrophages were exposed to LPS in the presence IgG or Ab1918 (1-180 mg/ml) and TNF in the media was analyzed 2 hour later by ELISA.

Example 9

Antibody 1918 Inhibits LPS-Induced HMGB1 Release from RAW 264.7

Figure 12A:
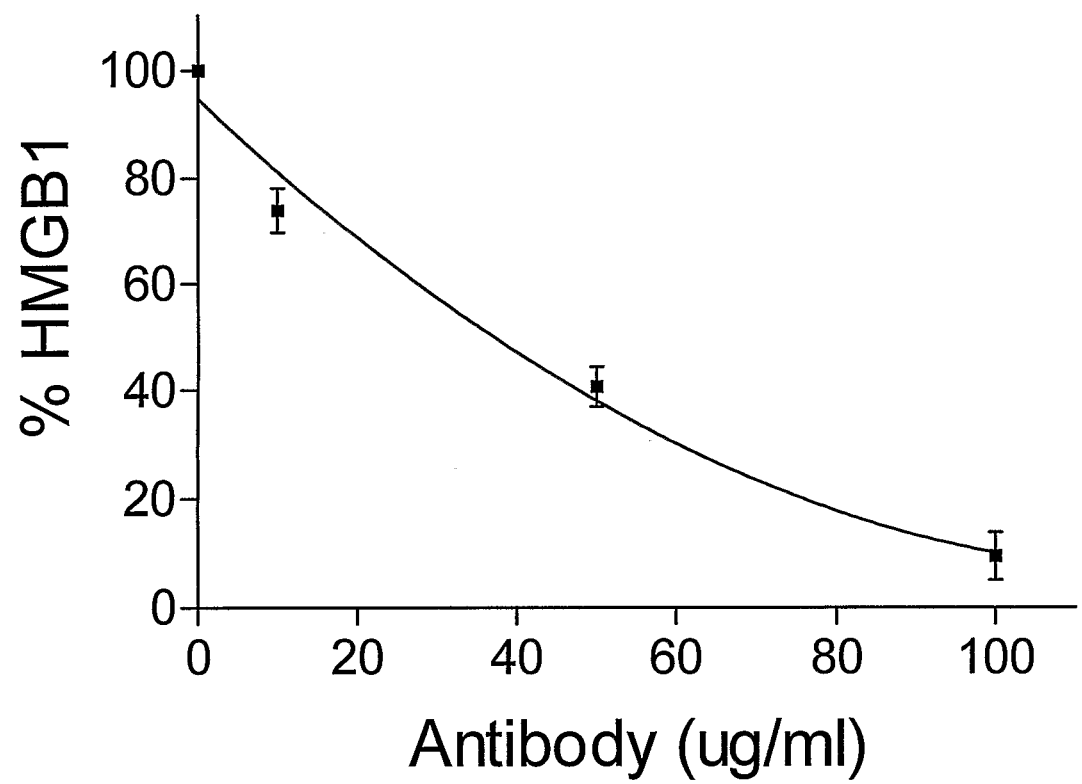
FIGS. 12A-B shows inhibition of HMGB1 levels in RAW 264.7 cells in plot and micrograph formats.
Figure 12B:
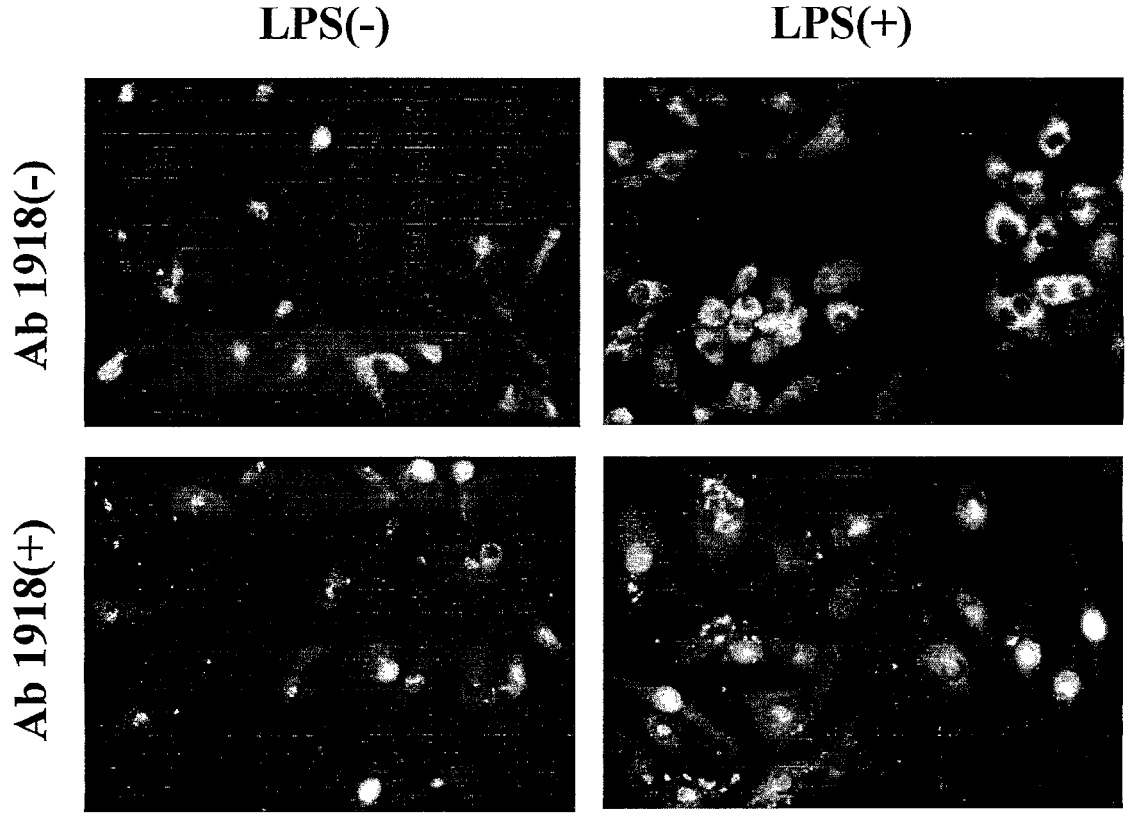

RAW cells were exposed to LPS in the presence or absence of Ab1918 (5-100 mg/ml). Secreted HMGB1 was determined from media 24 hours later by Western blot. Results are presented in FIG. 12A, which shows dose-dependent inhibition of HMGB1 production by Ab1918, and FIG. 12B, which shows a significant reduction in LPS-induced HMGB1 production by RAW 264.7 cells following treatment with Ab1918.

Example 9

Figure 13:
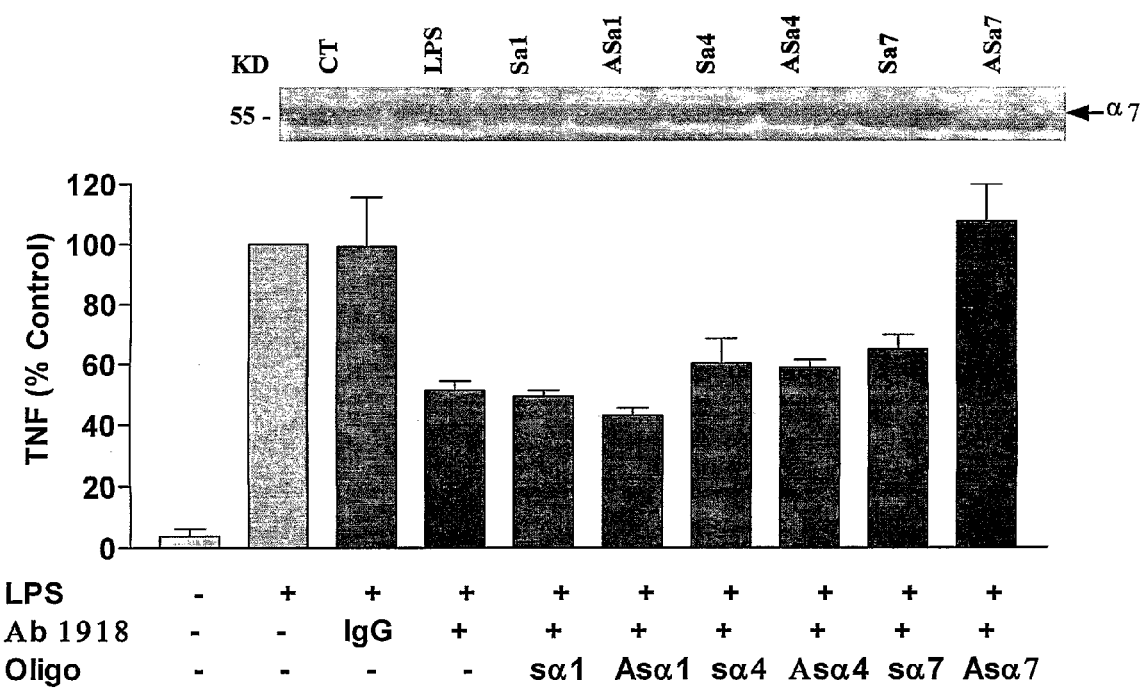
FIG. 13 is a bar plot indicating LPS-induced TNF production (as percent of control) in primary human macrophages, following treatment with antisense oligonucleotides to different subunits of acetylcholine receptors.

Antisense Oligonucleotides to α7 Subunit of Acetylcholine Receptor Inhibit the Effect of Ab1918 on TNF Release from Primary Macrophages To show that Ab1918 inhibits TNF release by binding the α7 subunit of acetylcholine (Ach) receptor, TNF release from LPS-stimulated primary human macrophages pretreated with antisense oligonucleotides to different subunits of Ach receptors was measured. The α7 subunit was detected by western blot using Ab1918 and TNF in the media was analyzed by ELISA. Results are presented in FIG. 13 which shows that when α7 subunit synthesis was inhibited by antisense oligonucleotides, treatment by Ab1918 did not reduce the TNF production, which remained on the level comparable to those of no antibody or irrelevant antibody treatments.

Example 10

Antibody 1918 Suppresses Systemic TNF in Endotoxemic Mice

Figure 14A:
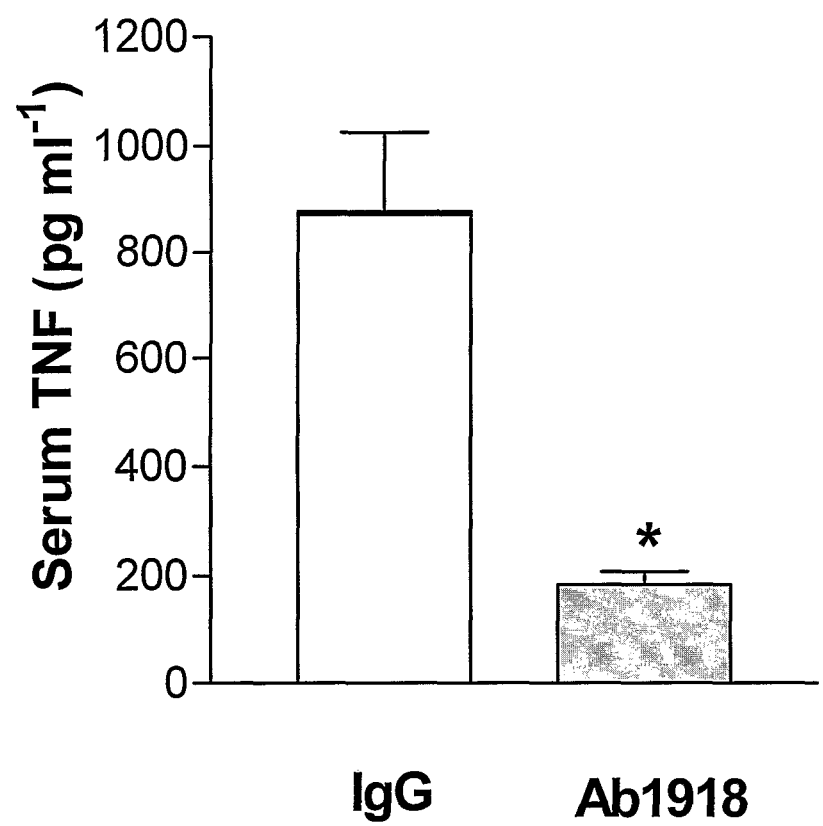
FIGS. 14A-B shows TNF levels in vivo in bar graph and micrograph formats.

Mice (n=11 per group) were treated introperitoneally (i.p.) with IgG (controls) or Ab1918 (7.2 mg/kg) 12 hour before LPS (7.0 mg/kg, i.p.) administration. Serum TNF levels were analyzed by ELISA in blood obtained 1.5 hours later (*P<0.05 versus controls). The results are presented in FIG. 14(A), which shows reduction in serum TNF levels following administration of Ab1918.

Figure 14B:
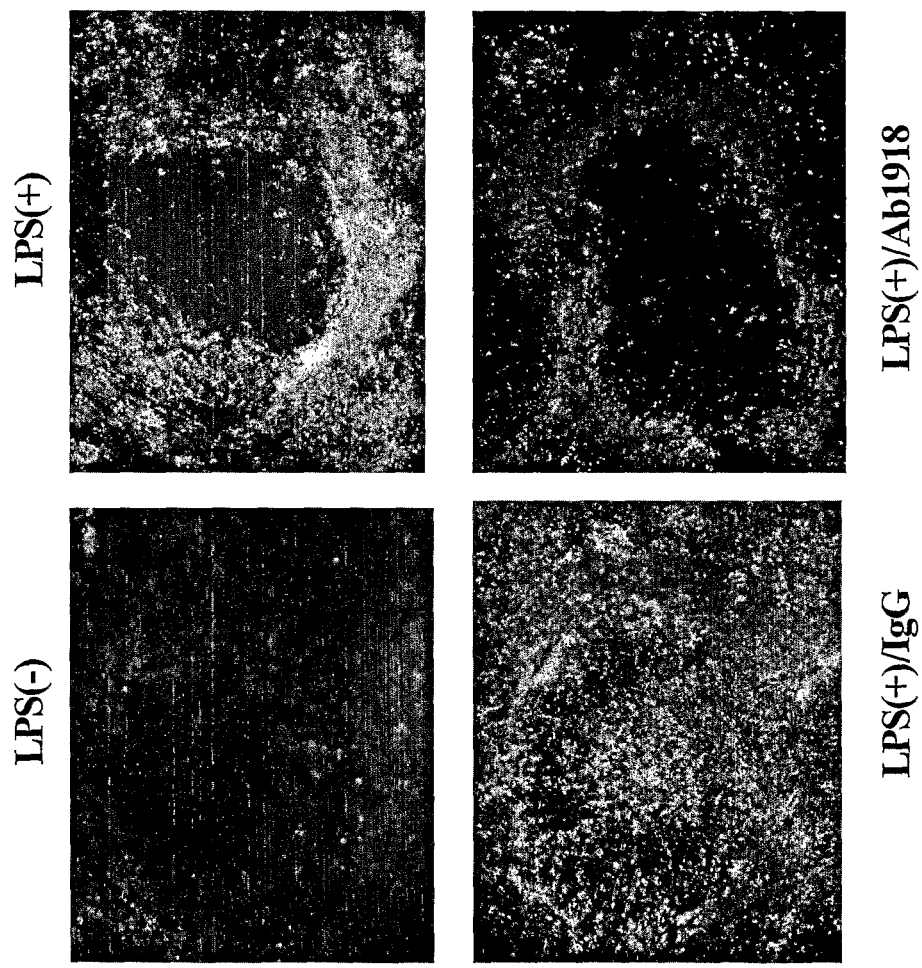

TNF levels in the spleen were analyzed 1.5 hours post LPS administration by immunostaining with anti-TNF antibodies. The results are presented in FIG. 14(B), which shows a significant reduction in LPS-induced TNF levels in spleens of mice treated with Ab1918.

Example 11

Figure 15A:
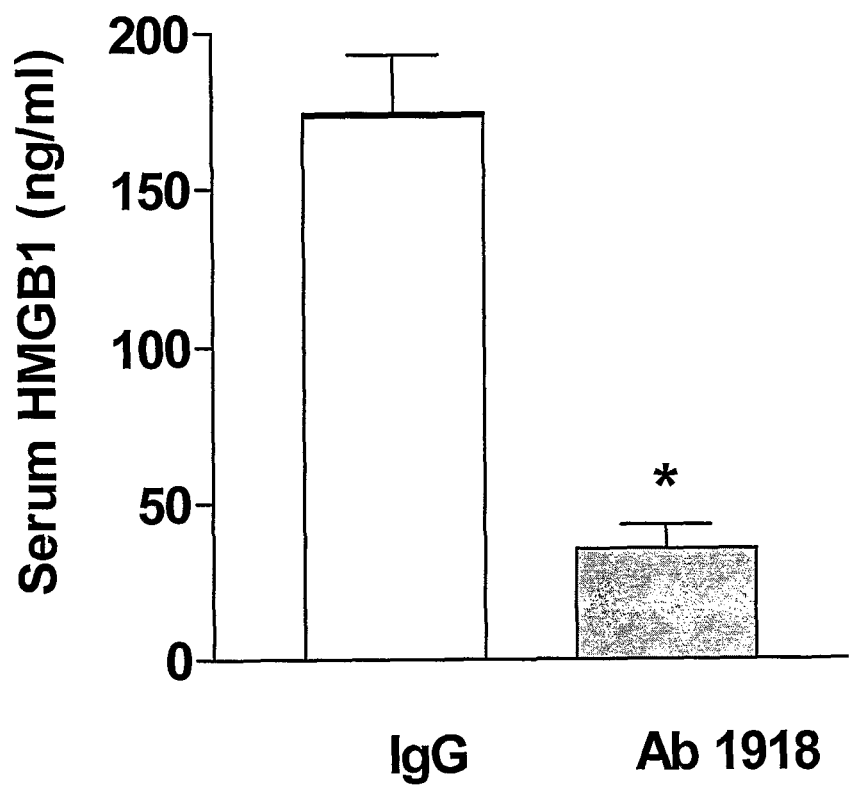
FIGS. 15A-B shows TNF levels, in vivo HMGB1 levels and survival rates in bar graph and plot formats.

Ab1918 Suppresses Systemic HMGB1 Level and Improves Survival of Mice with Cecal Ligation and Puncture-Induced Severe Sepsis Mice were treated i.p. with IgG (controls) or Ab1918 (n=7 per group) twice daily (7.2 mg/kg) for 2 days after cecal ligation and puncture (CLP). Serum HMGB1 was analyzed by Western blot (*p<0.05 versus controls). The results are presented in FIG. 15A, which shows a significant reduction in serum HMGB1 levels following treatment with Ab1918.

Figure 15B:
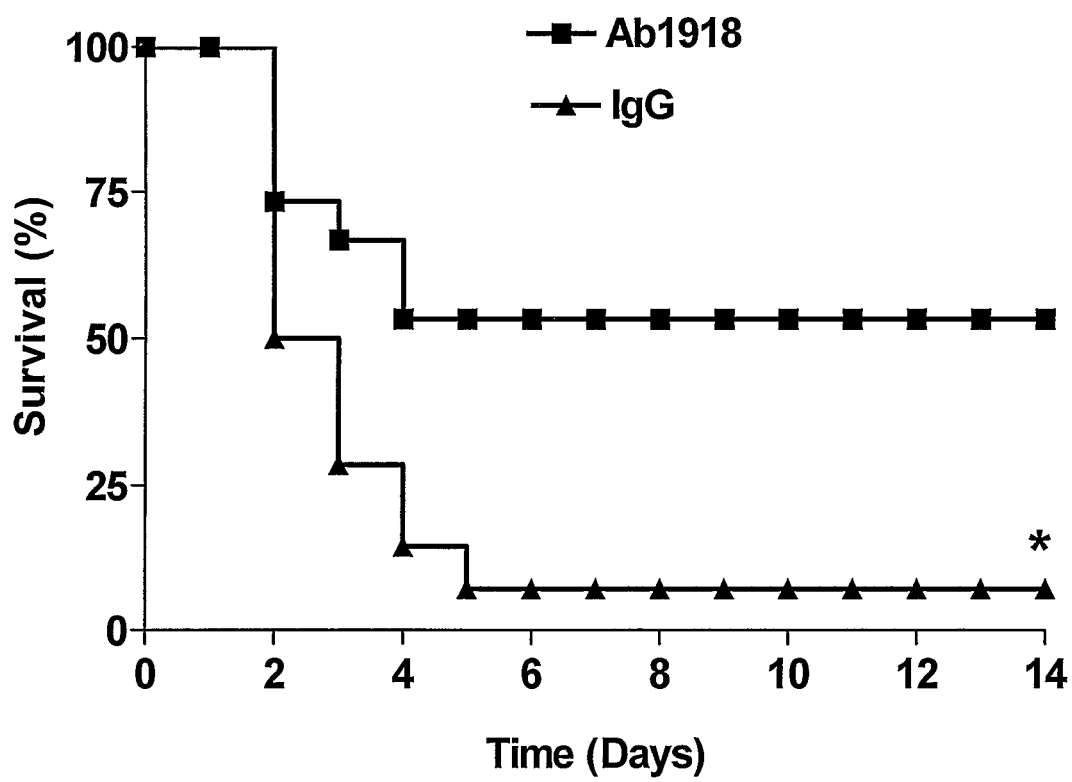

In survival experiments, mice (n=24) were treated with IgG or Ab1918 (7.2 mg/kg), for 3 days, beginning 24 hours after surgery (*P<0.0008 versus controls). The results are presented in FIG. 15B, which shows significant improvement in survival rates of mice treated with Ab1918 compared to mice that received sham treatment with an irrelevant IgG.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated antibody or an antigen-binding fragment thereof that specifically binds to a 20 amino acid peptide consisting of an amino acid sequence at least 90% identical to SEQ ID NO:2, 100% identical to SEQ ID NO:3, or at least 80% identical to SEQ ID NO:4.

2. The isolated antibody or antigen-binding fragment of claim 1 wherein the antibody or fragment specifically binds to a 20 amino acid peptide consisting of an amino acid sequence at least 90% identical to SEQ ID NO:2.

3. The isolated antibody or antigen-binding fragment of claim 1 wherein the antibody or fragment specifically binds to a 20 amino acid peptide consisting of the amino acid sequence of SEQ ID NO:3.

4. The isolated antibody or antigen-binding fragment of claim 1 wherein the antibody or fragment specifically binds to a 20 amino acid peptide consisting of an amino acid sequence at least 90% identical to SEQ ID NO:4.

5. The isolated antibody or antigen binding fragment of claim 1 wherein the antibody or fragment specifically binds to a peptide consisting of an amino acid sequence selected from the group consisting of SEQ ID NO:2, SEQ ID NO:3, and SEQ ID NO:4.

6. The isolated antibody or antigen-binding fragment of claim 1 wherein said antibody or fragment is human, humanized or chimeric.

7. The isolated antibody or antigen-binding fragment of claim 1 wherein said antibody or fragment is monoclonal.

8. The isolated antibody or antigen-binding fragment of claim 1 wherein said antibody or fragment is polyclonal.

9. The isolated antigen-binding fragment of claim 1 wherein said antigen-binding fragment is selected from the group consisting of an Fab fragment, an Fab' fragment, an F(ab)'$_2$ fragment and an Fv fragment.

10. The isolated antibody or an antigen-binding fragment thereof of claim 1, wherein the antibody or antigen binding fragment thereof specifically binds to a peptide consisting of SEQ ID NO:2.

11. The isolated antibody or an antigen-binding fragment thereof of claim 1, wherein the antibody or antigen binding fragment thereof specifically binds to a peptide consisting of SEQ ID NO:3.

12. The isolated antibody or an antigen-binding fragment thereof of claim 1, wherein the antibody or antigen binding fragment thereof specifically binds to a peptide consisting of SEQ ID NO:4.

13. A pharmaceutical composition comprising a pharmaceutically acceptable carrier or diluent and an antibody or an antigen-binding fragment thereof that specifically binds to a 20 amino acid peptide consisting of an amino acid sequence at least 90% identical to SEQ ID NO:2, 100% identical to SEQ ID NO:3, or at least 80% identical to SEQ ID NO:4.

14. The composition of claim 13 wherein said antibody or antigen-binding fragment specifically binds to a peptide consisting of an amino acid sequence selected from the group consisting of SEQ ID NO:2, SEQ ID NO:3, and SEQ ID NO:4.

15. The composition of claim 13 wherein said antibody or fragment is human, humanized or chimeric.

16. The composition of claim 13 wherein said antibody or antigen-binding fragment is monoclonal.

17. The composition of claim 13 wherein said antibody or antigen-binding fragment is polyclonal.

18. The composition of claim 13 wherein said antigen-binding fragment is selected from the group consisting of an Fab fragment, an Fab' fragment, an F(ab)'$_2$ fragment and an Fv fragment.

19. A pharmaceutical composition comprising a pharmaceutically acceptable carrier or diluent and an antibody or an antigen-binding fragment thereof that specifically binds to a peptide consisting of SEQ ID NO:2.

20. A pharmaceutical composition comprising a pharmaceutically acceptable carrier or diluent and an antibody or antigen-binding fragment thereof that specifically binds to a peptide consisting of SEQ ID NO:3.

21. A pharmaceutical composition comprising a pharmaceutically acceptable carrier or diluent and an antibody or antigen-binding fragment thereof that specifically binds to a peptide consisting of SEQ ID NO:4.

22. A method of treating a subject suffering from a cytokine-mediated inflammatory condition, wherein the level of cytokine release can be reduced by alpha-7 receptor activation, comprising:
  administering to said subject an effective amount of an antibody or an antigen-binding fragment thereof,
  wherein the antibody or the antigen-binding fragment specifically binds to a 20 amino acid peptide consisting of an amino acid sequence at least 90% identical to SEQ ID NO:2, 100% identical to SEQ ID NO:3, or at least 80% identical to SEQ ID NO:4, wherein the condition is selected from peritonitis, pancreatitis, sepsis, endotoxic shock, Crohn's disease, ulcerative colitis, adult respiratory distress syndrome, rheumatoid arthritis or asthma.

23. The method of claim 22 wherein said antibody or fragment specifically binds to a peptide consisting of an amino acid sequence selected from the group consisting of SEQ ID NO:2, SEQ ID NO:3, and SEQ ID NO:4.

24. The method of claim 22, wherein the mammal is a human.

25. The method of claim 22 wherein said antibody or antigen-binding fragment is human, humanized or chimeric.

26. The method of claim 22 wherein said antibody or fragment is monoclonal.

27. The method of claim 22 wherein said antibody or fragment is polyclonal.

28. The method of claim 22 wherein said antigen-binding fragment is selected from the group consisting of an Fab fragment, an Fab' fragment, an F(ab)'$_2$ fragment and an Fv fragment.

29. A method of treating a subject suffering from sepsis, comprising
  administering to said subject an effective amount of an antibody or an antigen binding fragment thereof, wherein said antibody or antigen-binding fragment specifically binds a peptide consisting of SEQ ID NO:2, thereby treating the sepsis.

30. The isolated antibody or antigen-binding fragment of claim 3, which specifically binds to a 20 amino acid peptide consisting of an amino acid sequence at least 95% identical to SEQ ID NO:2.

31. An isolated antibody that competes with, or inhibits, the antibody of claim 10 binding to SEQ ID NO: 2.

32. An isolated antibody that competes with, or inhibits, the antibody of claim 11 binding to SEQ ID NO: 3.

33. An isolated antibody that competes with, or inhibits, the antibody of claim 12 binding to SEQ ID NO: 4.

* * * * *

SEQUENCE LISTING

<160> NUMBER OF SEQ ID NOS: 4

<210> SEQ ID NO 1
<211> LENGTH: 502
<212> TYPE: PRT
<213> ORGANISM: Homo Sapiens -continued

```
<220> FEATURE:
<221> NAME/KEY: CHAIN
<222> LOCATION: (0)...(0)
<223> OTHER INFORMATION: The amino acid sequence of human alpha 7
      subunit of an nicotinic acetylcholine receptor deposited
      in GenBank under Accession Number P36544.

<400> SEQUENCE: 1

Met Arg Cys Ser Pro Gly Gly Val Trp Leu Ala Leu Ala Ala Ser Leu
 1               5                  10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Asn Leu Leu Gln Ile Met Asp
 50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Pro Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
        275                 280                 285

Ser Val Pro Leu Ile Ala Gln Tyr Phe Ala Ser Thr Met Ile Ile Val
290                 295                 300

Gly Leu Ser Val Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
            340                 345                 350

Val Arg Pro Ala Cys Gln His Lys Gln Arg Arg Cys Ser Leu Ala Ser
        355                 360                 365

Val Glu Met Ser Ala Val Ala Pro Pro Pro Ala Ser Asn Gly Asn Leu
370                 375                 380
```

```
Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
            405                 410                 415

Asp Glu His Leu Leu His Gly Gly Gln Pro Pro Glu Gly Asp Pro Asp
        420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
        450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
            485                 490                 495

Val Ser Lys Asp Phe Ala
            500

<210> SEQ ID NO 2
<211> LENGTH: 20
<212> TYPE: PRT
<213> ORGANISM: Homo Sapiens
<220> FEATURE:
<221> NAME/KEY: PEPTIDE
<222> LOCATION: (0)...(0)
<223> OTHER INFORMATION: A peptide corresponding to positions 31-50 in
      SEQ ID NO:1

<400> SEQUENCE: 2

Lys Glu Leu Val Lys Asn Tyr Asn Pro Leu Glu Arg Pro Val Ala Asn
1               5                   10                  15

Asp Ser Gln Pro
            20

<210> SEQ ID NO 3
<211> LENGTH: 20
<212> TYPE: PRT
<213> ORGANISM: Homo Sapiens
<220> FEATURE:
<221> NAME/KEY: PEPTIDE
<222> LOCATION: (0)...(0)
<223> OTHER INFORMATION: A peptide corresponding to positions 108-127 in
      SEQ ID NO:1

<400> SEQUENCE: 3

Trp Lys Pro Asp Ile Leu Leu Tyr Asn Ser Ala Asp Glu Arg Phe Asp
1               5                   10                  15

Ala Thr Phe His
            20

<210> SEQ ID NO 4
<211> LENGTH: 20
<212> TYPE: PRT
<213> ORGANISM: Homo Sapiens
<220> FEATURE:
<221> NAME/KEY: PEPTIDE
<222> LOCATION: (0)...(0)
<223> OTHER INFORMATION: A peptide corresponding to positions 204-223 in
      SEQ ID NO:1.
```

```
<400> SEQUENCE: 4

Lys Arg Ser Glu Arg Phe Tyr Glu Cys Cys Lys Glu Pro Tyr Pro Asp
1               5                   10                  15

Val Thr Phe Thr
            20
```